United States Patent [19]
Loosmore et al.

[11] Patent Number: 5,869,302
[45] Date of Patent: *Feb. 9, 1999

[54] ANALOG OF HAEMOPHILUS HIN47 WITH REDUCED PROTEASE ACTIVITY

[75] Inventors: Sheena M. Loosmore, Aurora; Yan-Ping Yang, Willowdale; Pele Chong, Richmond Hill; Raymond P. Oomen, Tottenham; Michel H. Klein, Willowdale, all of Canada

[73] Assignee: Connaught Laboratories Limited, Willowdale, Canada

[ * ] Notice: The term of this patent shall not extend beyond the expiration date of Pat. No. 5,506,139.

[21] Appl. No.: 487,167

[22] Filed: Jun. 7, 1995

Related U.S. Application Data

[63] Continuation-in-part of Ser. No. 296,149, Aug. 26, 1994, which is a continuation-in-part of Ser. No. 278,091, Jul. 21, 1994, Pat. No. 5,506,139.

[51] Int. Cl.$^6$ .............................. C12N 9/52; C12N 15/31; C12N 15/57
[52] U.S. Cl. ................... 435/172.1; 435/220; 435/320.1; 435/252.3; 435/325; 435/419; 935/10; 935/14; 536/23.2; 536/23.7
[58] Field of Search ............................... 435/220, 320.1, 435/252.3, 172.1, 325, 419; 536/23.2, 23.7; 935/10, 14

[56] References Cited

FOREIGN PATENT DOCUMENTS

| | | |
|---|---|---|
| WO 94/12641 | 6/1992 | WIPO . |
| WO 92/10936 | 7/1992 | WIPO . |
| WO 92/11367 | 7/1992 | WIPO . |
| WO 94/00149 | 1/1994 | WIPO . |

OTHER PUBLICATIONS

Zangwill et al, 1993 MMWR 42:1–15.
Schoendorf et al, 1994 Pediatrics 93:663–8.
Brenner S., 1988 Nature 334:528–530.
O'Hagan 1992 Clin. Pharmokinet. 22:1–10.
Ulmer et al, 1993 Curr. Opinion. Invest. Drugs 2:983–989.
Chang et al, 1978 Nature 275:617–624.
Goeddel et al 1980 Nucl. Acid. Res. 8:4057–4074.
Harkness et al, 1992 J. Bacteriol. 174:2425–2430.
Loeb M.R., 1987 Infec. Immun. 55:2612–2618.
Holmes and Quigley 1981. Analyt. Biochem. 114:193–197.
Young and Davis, 1983 Proc. Natl. Acad. Sci. USA 80:1194–1196.
Panezzutti et al, 1993 Infec. Immun. 61:1867–1872.
Lipinska et al, 1985 Bacteriol. 171:1574–1584.
Barenkamp et al, 1986 Infect. Immun. 52:572–578.
Crowl et al, 1985 Gene 38:31–38.

*Primary Examiner*—Keith D. Hendricks
*Attorney, Agent, or Firm*—Sim & McBurney

[57] ABSTRACT

An isolated and purified analog of *Haemophilus influenzae* Hin47 protein has a decreased protease activity which is less than about 10% of that of natural Hin47 protein and preferably substantially the same immunogenic properties as natural Hin47 protein. An isolated an purified nucleic acid molecule encoding the Hin47 analog may be provided in a recombinant plasmid which may be introduced into a cell which is grown to produce the Hin47 analog. Immunogenic compositions comprising the Hin47 analog and the encoding nucleic acid may be formulated as vaccines for in vivo administration to a host, including a human, to confer protection against diseases caused by a bacterial pathogen, including Haemophilus species, such as *Haemophilus influenzae*, that produces Hin47 protein or a protein capable of inducing antibodies in the host specifically reactive with Hin47 protein. The Hin47 analog and the encoding nucleic acid also may be employed in diagnostic applications.

44 Claims, 26 Drawing Sheets

FIG. 2A
SB33 Hin47 sequence

```
GGATCCGTTAATACTGAAATAAATGGCACACCTTTTTCACGCATTTGGGCAAGTACAGCA
         10        20        30        40        50        60

CTGGTTTTGCCATTTGCATTAAAGAGAATAATGCTTCCTGCATACGAGCACCACCACTC
         70        80        90       100       110       120

GCAGAGAAACATACAAAACGGACAATTCATTTCCATCGCTTTTTCAGCCGCTTTAACAAAT
        130       140       150       160       170       180

TTTGCACCAACTACAGAACCCATTGAACCGCCCATAAAAGCAAAGTTCGATGCAGCCACA
        190       200       210       220       230       240

ACAATTGGCATATCATAAAGTGTACCTGTCATAGTAATTAGCGCATCTTTCTCGCCCGTT
        250       260       270       280       290       300

TCTTTTTGTGCCCGCATTGATACGATCTTTATATTTCTTTAAATCTTTAAAATTTTAAAATA
        310       320       330       340       350       360
```

FIG. 2B

```
TCTTTTGGTTCTAAATCTGCCGCAATTTCTTGGCTTGAATCTTCGTCCAATAAATTTAAT
        370       380       390       400       410       420

AAACGCTCACGAGCATCAATACGCATATGATGACCACATTTCGGGCAAACATACAGATTA
        430       440       450       460       470       480

CGTTTGAGTTCTTCACTATAAAGTACTTGTTCACAAGCAGTACATTTTGTCCATACGCCT
        490       500       510       520       530       540

TCTGGCACATTGGCTTTTCGAGTGGGAAGAAGGACTTTTACTAAAAATTCGGTTAATC
        550       560       570       580       590       600

CAGCTCATTTTTTGACCTTTTTATTGACTAGAAAAATTGCGCGTATTAGAACATAAATTTA
        610       620       630       640       650       660

TAGAATTTGCTACTTGTAAGACCCGTTTTTTGTACTGCTCCGATTTCCTTTTAAACAAGATA
        670       680       690       700       710       720

ATTTGCTCTCCTCTTATTGAACATTTTTTTATTTTTGTCTTACTGACCACGTTATCT
        730       740       750       760       770       780
```

FIG. 2C

```
                          met lys lys thr arg phe val leu asn ser ile ala leu
                          MET LYS LYS THR ARG PHE VAL LEU ASN SER ILE ALA LEU
GAAATTATTTTGGAGTATTTATGAAAAAACACGTTTTGTACTAAATAGTATTGCACTT
                          atgaaaaaacacgttttgtattaaatagtattgcactt
         790            800            810           820           830          840 gly leu ser val leu ser thr ser phe val ala gln ala thr leu pro ser phe val ser
GLY LEU SER VAL LEU SER THR SER PHE VAL ALA GLN ALA THR LEU PRO SER PHE VAL SER
GGATTAAGTGTATTAAGCACATCATTTGTTGCTCAAGCCACTTTGCCAAGTTTTGTTTCG
gg
    850           860           870           880           890           900 glu gln asn ser leu ala pro met leu glu lys val gln pro ala val val thr leu ser
GLU GLN ASN SER LEU ALA PRO MET LEU GLU LYS VAL GLN PRO ALA VAL VAL THR LEU SER
GAACAAAACAGTCTTGCCACCAATGTTAGAAAAGTACAACCTGCCGTTGTCACTCTTTCC
    910           920           930           940           950           960 val glu gly lys ala lys val asp ser arg ser pro phe leu asp ser ile pro glu glu
VAL GLU GLY LYS ALA LYS VAL ASP SER ARG SER PRO PHE LEU ASP SER ILE PRO GLU GLU
GTTGAAGGAAAAGCTAAAGTAGATTCTCGTTCTCCTTTCCTAGACGATATTCCTGAAGAA
    970           980           990          1000          1010          1020 phe lys phe phe phe gly asp arg phe ala glu gln phe gly gly arg gly glu ser lys
PHE LYS PHE PHE PHE GLY ASP ARG PHE ALA GLU GLN PHE GLY GLY ARG GLY GLU SER LYS
TTTAAATTCTTCTTTGGCGATCGTTTTGCCGAACAATTTGGTGGACGTGGAGAATCAAAG
   1030          1040          1050          1060          1070          1080
```

FIG. 2D

```
ARG ASN PHE ARG GLY LEU GLY SER GLY VAL ILE ILE ASN ALA SER LYS GLY TYR VAL LEU
CGTAACTTCCGTGGTTTAGGTTCTGGTGTCATTATTAATGCAAGCAAAGGCTATGTTTTA
    1090           1100          1110          1120          1130          1140

THR ASN ASN HIS VAL ILE ASP ALA GLU LYS ILE THR VAL GLN LEU GLN ASP GLY ARG
ACCAATAATCATGTTATTGATGAAGCTGATAAAATTACCGTGCAATTACAAGATGGGCGT
    1150          1160          1170          1180          1190          1200

GLU PHE LYS ALA LYS LEU VAL GLY LYS LEU SER ASP GLU LEU VAL GLN LEU
GAATTTAAAGCAAAATTAGTGGGTAAAGATGAACTATCAGATGCATTAGTACAGCTT
    1210          1220          1230          1240          1250          1260

GLU LYS PRO SER ASN LEU THR GLU ILE LYS PHE ALA ASP SER ASP LYS LEU ARG VAL GLY
GAAAAACCAAGTAATTTAACAGAAATCAAATTTGCTGATTCCGACAAATTACGCGTAGGC
    1270          1280          1290          1300          1310          1320

ASP PHE THR VAL ALA ILE GLY ASN PRO PHE GLY LEU GLY GLN THR VAL THR SER GLY ILE
GATTTCACTGTTGCAATCGGTAATCCATTTGGTTTAGGTCAAACTGTGACATCAGGTATT
    1330          1340          1350          1360          1370          1380

VAL SER ALA LEU GLY ARG SER THR GLY SER ASP SER GLY THR TYR GLU ASN TYR ILE GLN
GTTTCTGCATTGGGTCGTTCAACAGGTTCTGACAGTGGCACTTATGAAAACTATATTCAA
    1390          1400          1410          1420          1430          1440

ASP ALA ALA VAL ASN ARG GLY ASN SER GLY GLY ALA LEU VAL ASN LEU ASN GLY GLU
ACCGATGCAGCAGTAAACCGCGGTAATTCGGGTGGAGCCGTTAGTAAACTTAAATGGCGAA
    1450          1460          1470          1480          1490          1500
```

FIG.2E

```
LEU ILE GLY ILE ILE ASN THR ALA ILE ILE SER PRO SER GLY GLY ASN ALA GLY ILE ALA PHE
CTTATTGGAATTAATACCGCAATTATTTCTCCAAGCGGTGGCAATGCAGGAATTGCCTTT
            1510              1520              1530              1540              1550              1560

ALA ILE PRO SER ASN GLN ALA SER ASN LEU VAL GLN GLN ILE LEU GLU PHE GLY GLN VAL
GCGATTCCAAGTAATCAAGCAAGCAATTTAGTGCAACAAATTTTAGAATTTGGTCAAGTG
            1570              1580              1590              1600              1610              1620

ARG ARG GLY LEU LEU GLY ILE LYS GLY LEU GLY GLU ASN ALA ASP LEU ALA LYS ALA PHE
CGTCGCGGATTGCTTGGTATTAAAGGTTTGGGCGAACTCAATGCTGATTTAGCCAAAGCCTTT
            1630              1640              1650              1660              1670              1680

ASN VAL SER ALA GLN GLN GLY ALA PHE VAL SER GLU VAL LEU PRO LYS SER ALA ALA GLU
AATGTAAGCGCGCAACAAGGCGCATTTGTAAGTGAAGTTTTACCGAAAATCTGCTGAA
            1690              1700              1710              1720              1730              1740

LYS ALA GLY LEU LYS ALA LYS ALA GLY ASP ILE ILE THR ALA MET ASN GLY GLN LYS ILE SER SER
AAAGCAGGACTTAAAGCGGGCGATATTATCACGGCGATGAACGGTCAAAAATCTCAAGT
            1750              1760              1770              1780              1790              1800

PHE ALA GLU ILE ARG ALA LYS ILE ALA THR THR GLY ALA GLY LYS GLU ILE SER LEU THR
TTCGCTGAAATTCGTGCAAAATCGCAACCACTGGTGCAGGCAAAGAGATTAGCTTGACT
            1810              1820              1830              1840              1850              1860
```

FIG. 2F

| TYR | LEU | ARG | ASP | GLY | LYS | SER | HIS | ASP | VAL | LYS | MET | LYS | LEU | GLN | ALA | ASP | ASP | SER | SER |
|---|---|---|---|---|---|---|---|---|---|---|---|---|---|---|---|---|---|---|---|

TACTTACGTGATGGCAAATCCCACGACGTTAAAATGAAATTACAAGCGGATGATAGTAGC
           1370              1880              1890              1900              1910              1920

| GLN | LEU | SER | SER | LYS | THR | GLU | LEU | PRO | ALA | LEU | ASP | GLY | ALA | THR | LEU | LYS | ASP | TYR | ASP |
|---|---|---|---|---|---|---|---|---|---|---|---|---|---|---|---|---|---|---|---|

CAACTTTCCTCAAAAACTGAGTTGCCCTGCATTAGATGGTGCAACATTGAAAGACTACGAT
           1930              1940              1950              1960              1970              1980

| ALA | LYS | GLY | VAL | LYS | SER | LYS | GLY | ILE | GLU | ILE | LYS | ILE | THR | GLN | PRO | ASN | SER | LEU | ALA | ALA | GLN |
|---|---|---|---|---|---|---|---|---|---|---|---|---|---|---|---|---|---|---|---|---|---|

GCTAAAGGCGTTAAAAGGAATTGAAAATCACAAAAATTCAACCTAATTCGGCTGCACAA
           1990              2000              2010              2020              2030              2040

| ARG | GLY | LEU | LYS | SER | GLY | ASP | ILE | ILE | ILE | GLY | ILE | ASN | ARG | GLN | MET | ILE | GLU | ASN | ILE |
|---|---|---|---|---|---|---|---|---|---|---|---|---|---|---|---|---|---|---|---|

CGTGGGTTTAAAATCGGGCGATATTATTATTGGTATTAATCGTCAAATGATCGAAAACATT
           2050              2060              2070              2080              2090              2100

| ARG | GLU | LEU | ASN | LYS | VAL | LEU | GLU | THR | GLU | PRO | SER | ALA | VAL | ALA | LEU | ASN | ILE | LEU | ARG |
|---|---|---|---|---|---|---|---|---|---|---|---|---|---|---|---|---|---|---|---|

CGTGAATTAAATAAAGTGCTTGAAACTGAAACCGTCAGCAGTTGCACTTAATATTTTACGA
           2110              2120              2130              2140              2150              2160

| GLY | ASP | SER | ASN | PHE | TYR | LEU | LEU | LEU | VAL | GLN | *** |
|---|---|---|---|---|---|---|---|---|---|---|---|

GGTGACAGTAATTTCTATTTATTAGTGCAATAATCTGCTTGATATATTTAAGAAAAAAGT
           2170              2180              2190              2200              2210              2220

FIG.2G

```
CCGATCACACAATGATCGGGCTTCTTTTATGCAGCAATCGTTCTTAACAAATCCACCACAA
         2230         2240         2250         2260         2270         2280

ATTCTAACCGCACTTTGTTATCAGATAAATCTTTCATGAACTTAAATTTAATGGGCCAT
         2290         2300         2310         2320         2330         2340

CAAATCGATACACAATAGGTTCTTTTTGAATTAATTGAATAAATTTATCTGGATTCACTT
         2350         2360         2370         2380         2390         2400

GTGCTTTTGCTGAAAAACTCAATAAAAACCGCCTTGTGTTCCTGCATCAATTCGCACAACTT
         2410         2420         2430         2440         2450         2460

TCAACGGCTCAACCAACAAACGCAATTCTGCAATTTGCAGTAAAATTTTTGTTGCATCAG
         2470         2480         2490         2500         2510         2520

GCAATAAATCCGAATCGATCTATTAACTCAACTTTTAATTCATCTAATTCTGCTTTACTCT
         2530         2540         2550         2560         2570         2580

CTGCTGCAGCAATGCGTTTATAAAAGGATAAACGCATATTCACGTCTCCTAGATAATCAT
         2590         2600         2610         2620         2630         2640
```

FIG.2H

```
CAGGCAGTAAAGCAGGCACACGCAATTCAATATCCGCTTGTTGCGTCAATTCTTCTA
      2650          2660          2670          2680          2690          2700

ATGATGGTTCACGCCCCTTCTTTTAACGCTTTAACCGCTGCATCCAATAATTCCATATAAA
      2710          2720          2730          2740          2750          2760

GCGAAAACCGATGCTTTCAATTTGTCCACTTTTGTTTCGTTTCCAAGTAATTCGCCGGCAC
      2770          2780          2790          2800          2810          2820

CACGAATCTCTAAATCGTGGGTTGCCCAAGATAAAACCAGCCCCAAGATTATCAAGATTTT
      2830          2840          2850          2860          2870          2880

CCAACGCATCTAGA
      2890
```

FIG. 3A

Comparison of Hin47 with E.coli htrA and S. typhimurium htrA

```
MKKTIRFVINSTAIGLS---VLS-TSFVAQATLPSFVSEQ--NSLAPMLEKVQP              Hin47
....TLA.SRL..S..--LA..PL.AT.AE.-S.ATTA.QMP.........M.              E. coli
--T.AMS.A..LGLA..PL.AT.AE.SS.AMTA.QMP.........M.                   S. typh AVVILSVEGKAKV-DSRSP------FLDDIP--EEFKFFFGDRF--A       Hin47
              S..SIN...STT.NTP.M.RNFQQF.G..S.FCQ.GSP.QSSP.CQG       E. coli
              S..SIN...STT.NTP.M.RNFQQF.G..S.FCQDGSP.QNSP.CQG       S. typh
                                           —                —

EQFGGRGESKRNFRGIGSGVIINASKGYVLTNNHVIDEADKITVQLQDGREFK              Hin47
G.G.NG.GQQK.MA.......D.D...V......V.N.TV.K...S...K.D              E. coli
GGN.GN.GQQK.MA.......D.A...V......V.N.SV.K...S...K.D              S. typh
                                 —

AKLVGKDELSDIALVQLEKPSNLTEIKFADSKLRVGDFTVAIGNPF           Hin47
            ..M.....PR.....I.IQN.K...A.M.....A....Y.G......           E. coli
            ..V.....PR.....I.IQN.K...A.L...A....Y........           S. typh
                                                 —

GLGQTVTSGIVSALGRSIGSDSGTYENYIQLTDAAVNRGNSGGALVNLNGELIG            Hin47
...E.........---.LNAEN...F.....I............                       E. coli
...E.........---.LNVEN...F.....I............                       S. typh
```

FIG. 3B

```
INTAIISPSGNAGIAFAIPSNQASNLVQQILEFGQVRRGLLGIKGG      Hin47
....LA.D..I.G.....MK..TS.MV.Y...K..E...M.T         E. coli
....LA.D..I.G.....MK..TS.MV.Y......E...M.T         S. typh EINADLAKAFNVSAQQGAFVSEVLPKSAAEKAGLKAGDITAMNQKISSFAE
...SE.....MK.D.R.....Q...N.S.A...I.....A           E. coli
...SE.....MK.D.R.....Q.M.N.S.A...I.....A           S. typh IRAKIATTGAGKEISLTYLRDGKSHDMKMLQADDSSQLSSKTELPA      Hin47
L..QVG.MPV.SKLT.GL.....QVN.NLE..QSSQN.VD.SSIFNG    E. coli
L..QVG.MPV.SK.....GL..E..AIT.NLE..QSSQ..VD.S.IFSG  S. typh LDGA--TLKDYDAKGVKGIETIKIQPNSLAAQRGLKSGDIIGINRQMIENLR  Hin47
IE..EMSN.GK.QGV.VNNK.----GTP...I...K.V...A.Q.AVK..A  E. coli
IE..EMSN.GQ.KGV.VSSVKA----.P...I...K.V...A.Q.PVK..A  S. typh EINKVLETEPSAVAINILRGDSNFYLLVQ*                      Hin47
..R..DSK..VL.....Q....--RH.P.N*                    E. coli
..R.I.DSK..VL.:..Q....SI...M.*                     S. typh
```

FIG. 4A

```
TCN    :              IVGGYKCEKNSQPWQVAVIN------E----YLCGG VLID
PKAAB  :              IIGGRECEKNSHPWQVAIYHY----SS--FQCGG VLVN
PTN    :              IVGGYTCGANIVPYQVSLN-----SGY--HFCGG SLIN
CHAA   :              IVNGEEAVPGSWPWQVSLQDK---TGF--HFCGG SLIN
EST    :              VVGGTEAQRNSWPSQISLQYRSGSSWA--HICGG TLIR
RP2A   :              IIGGVESIPHSRPYMAHLDIV--TEKGLRVICGG FLIS
SGT    :              VVGGIRAAQGEFPFMVRLSM----------GCGG ALYA
SGBE   :              ISGG---------DAIYSS---------TGRCSIGFNVRSGS
SGA    :              IAGG---------EATTIG---------GSRCSIGFNVSVNG
ALP    :              ANIVGG-------IEYSIN---------NASLCSVGFSVTRGA
hin47  :              AEQFGG       RGESKR         N FRGLGGVIINAS
                      ******                            **
con                   <------>          <---->          <----->

# (His57)
TCN    : ------PSWVITAAHCY--S----N-NYQ-VLLGRNNLFK-DEPFAQRRLV
PKAAB  : ------PKWVLTAAHCK--N----DNYEV-WL-GRHNLFENENT-AQFFGV
PTN    : ------SQWVVSAAHCY--X----SGIQV-RL-GEDNINVEGN-EQFTSA
CHAA   : ------ENWVVTAAHCG--V----TTSDV-VVAGEFDQGSSSEK-IQKLKI
EST    : ------QNWMIAAHCV--D----RELTFRVVGEHNLNQNGT-EQYVGV
RP2A   : ------RQFVLTAAHCK-------GREIT-VILGAHDVRKREST-QQKIKV
SGT    : ------QDIVLTAAHCV--SGSGNNISIT-AIGGVVDL-QSG-A-AVKVRS
```

FIG. 4B

```
SGBE  :                    TYYFLTAGHCT--D------GATT-WVA------------NS-ARITVL
SGA   :                    VAHALTAGHCT--------NISASW------------------SI
ALP   :                    TKGFVTAGHGTVN------AT-AR-IG------------GAVVG
Sal.T :                    KGYVVINHVDNASVIKQLSDGR
hin47 :                    KGYVLINNHVIDEA     DK-IT-VQ------------LQDGRE
                           ********
con        <---------------->                  <---X--------->
```

```
                                                  # (Asp102)
TCN   : RQS-FRHPDYTPLI  PVHDH---SNDIMLHLSEPADITGGMKV-------------
PKAAB : TAD-FPHPGFNLSAD-GKDY---SHDIMLRLQSPAKITDAVKV-------------
PIN   : SKS-IVHPSYN-----------SNTL---NNDIMLIKLKSAASLNSRVAS-------
CHAA  : AKV-FKNSKYN-----------SLTI---NNDITLIKLSTAASFSQIVSA-------
EST   : QKI-VVHPYVN-----------TDDVAAGYDIALIRLAQSVTLNSYVQL--------
RP2A  : EKQ-IIHESYN-----------SVFN---LHDIMLJKLEKKVEJTPAVNV-------
SGT   : TKV-LQAPGYN-----------G-T----GKDWALIKLAQPIN-----QPT------
SGBE  : GTT-SGS-SF-------------------PNNDYGIVRYINTITPX  DGIVG----
SGA   : GTR-TGT-SF-------------------PNNDYGIIRHSNPAAA  DGRVYLNGS--
ALP   : -TFAARV--F-------------------PGNDRAWSLTSAQIL--  LPRVANGSS--
hin47 : FKAKLVG         KDEL         SDIALVQLEKPSNL    TEIKFADSDKLRVGDF
                                    ***********
con        <---X-----><-----------> <-----><-----------> <------>
```

FIG. 4C

```
TCN    : ----IDLPT--KEPKVGSTCLASGWGSTNPS-E-MVVSHDLQCVNIHLLSN
PKAAB  : ----LELPT--QEPE-LGSICEASGWGSIEPGPDFEFPDEIQCVQLTLLQN
PIN    : ----ISLPT--SCAS-AGIQCLISGWGNIKSS--GTSYPDVLKCLKAPILSD
CHAA   : ----VCLIPSASDFAAGTICVTIGMLTRY--¦-ANTPDRLQQASLPLLSN
EST    : ----GVLPRAGTILANNSPCYITGWGLTR-T--NGQLAQTLQQAYLPTVDY
RP2A   : ----VPLPSPSDFTHPGAMCWAAGMGKIGVR---DPT-SYTLREVELRIMDE
SGT    : ----LKIAT--TTAYNQGIFTVAGMGANRE----GGSQQRYLLKANVPFVSD
SGBE   : GQDITSAA   NATVGMAVIRRGSTI-----------GIHSGSVTAL
SGA    : YQDITTAG   NAFVGQAVQRSGSTI-----------GLRSGSVIGL
ALP    : FVIVRGST---EAAVGAAVCRSGRIT-----------GYQCGTITAK
hin47  : TVAIGNPFGLGQTVTSGIVSALGRST           GSDSGTYENY
                                            ****
con             ------>      <-------->    <---->

TON    : EKCIE--TYKINVT-DMLCA-G-E---MEGGK-DICA--GDSGGPLIC--
PKAAB  : TFCAD--AHPDKVT-ESMLCAGY-L----P--GGKDTCM--GDSGGPLIC--
PIN    : SSCKS--AYPGQIT-SMFCAGY-L----E--GGKDSCQ--GDSGGPVVC--
CHAA   : TNCKK--YWGIKIK-DAMICA-G-A---S--GV-SSCM--GDSGGPLMC--
EST    : AICSSSSYMGSIVK-NSMVCA-G-G---D--GVRSGCQ--GDSGGPLHC--
RP2A   : KACVDYRYEYKF----QVCV-GSP---T--TLRAAFM--GDSGGPLIC--
SGT    : AACRS--AYGNELVANEEICA-G-YPDIG--GV-DTCQ--GDSGGMFR--
SGBE   : NATVN--YGGGDVV-YGMIRT-N-------------VCAEPGDSGGPLYS--
                                              # (Ser195)
```

FIG. 4D

```
SGA    : NATVN--YGSSGIV-YGMIQT-N-----------------VCAQPGDSGSLFA-
ALP    : NVTAN--Y-AEGAV-RGLTQG-N-A---------CMGR--GDSGGSWITS
hin47:                                  IQT D A      AVNR  GNSGGALVNLN
                        *** * *         ****        ********
con                                <---> <-><-->

TQN    : D--------GVLQGITSGGA-TP-------C-A-KP--K-T-PAIYAKLIKFT-SW
PKAAB  : NG--------MMQGITSMGH-TP-------C-GSA---N-K-PSIYKLIFYL-DW
PIN    : SGK-------LQGIVSMGS--G--------C-AQK---N-K-PGVYTKVCNYV-SW
CHAA   : KKN-GAWILVGIVSMGS-ST----------C-S-T---S-T-PGVYARVTALV-NW
EST    : LVN-GQYAVHGVTSF-VSRLG---------C-NVT---R-K-PIVFTRVSAYI-SW
RP2A   : --A-GV--AHGIVSYG--------------HPD----A-KPPALFTRVSTYV-PW
SGT    : KDNADEMIQVGIVSMGY--G----------C-A-R---PGY-PGVYTEVSTFA-SA
SGBE   : G---------TRAIGLTSGGS-GN------C-S-S---G-G-TTFFQPVTEALVAY
SGA    : G---------STALGLTSGGS-GN------C-R-T---G-G-TTFYQPVTEALSAY
ALP    : A---------GQAQGMSGGN-VQSNGNCG-IPASQ-R-SSLFERLQPIL-SQ
hin47:         GELIGINTAII SP SGGNAG IAFAI P SNQASNLVQIL
                            ????
con    >                                    <------><----X<----
```

FIG. 4E

TON   : IKKMKENP
PKAAB : IDDITENP
PIN   : IKQTTASN
CHAA  : VQQILAAN
EST   : INVIASN
RP2A  : INAVIN
SGT   : IASAARIL
SGBE  : GVSVY
SGA   : GAIVL
ALP   : YGLSLVTG
hin47 : EFQQMRRGLLGIKG
con   : ------>

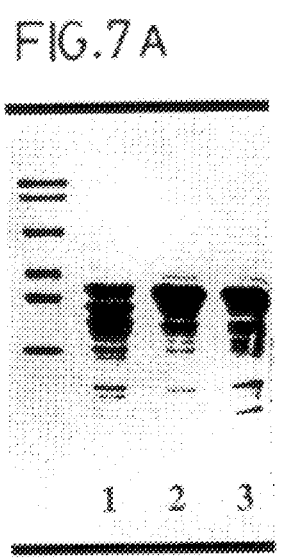  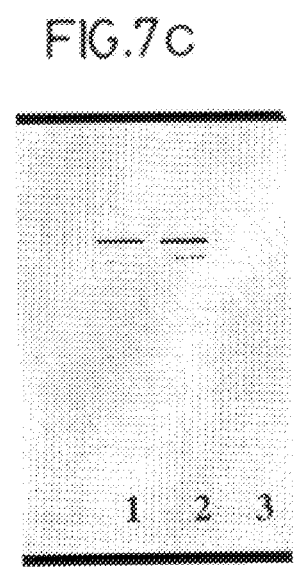

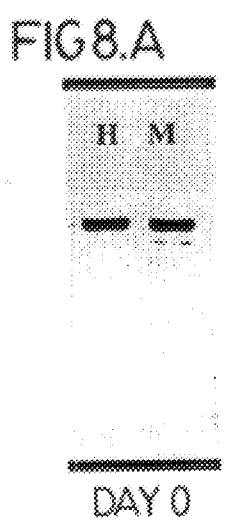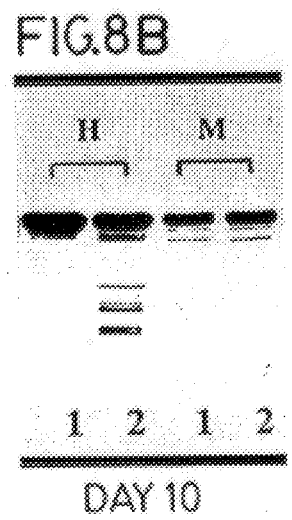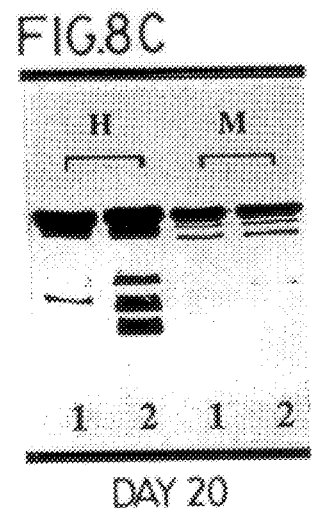

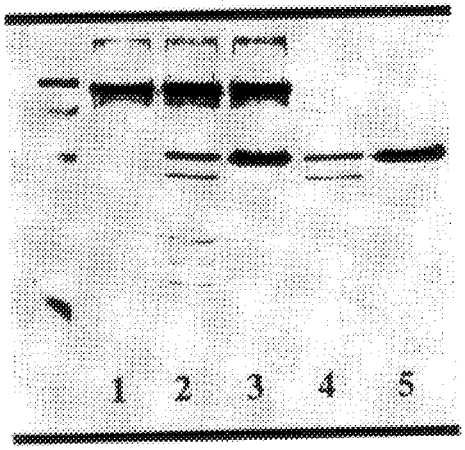
FIG. 9A Day 0
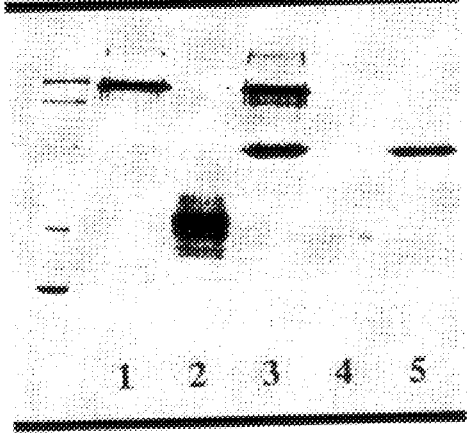
FIG. 9B 1-week
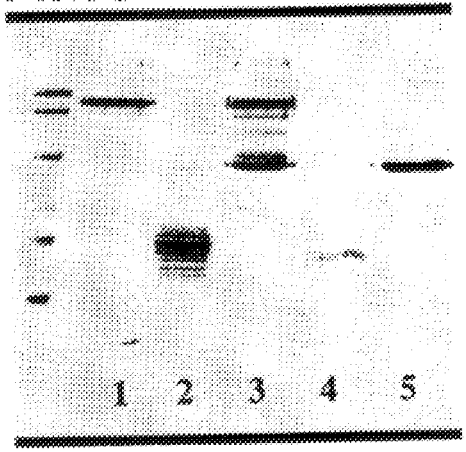
FIG. 9C 2-week
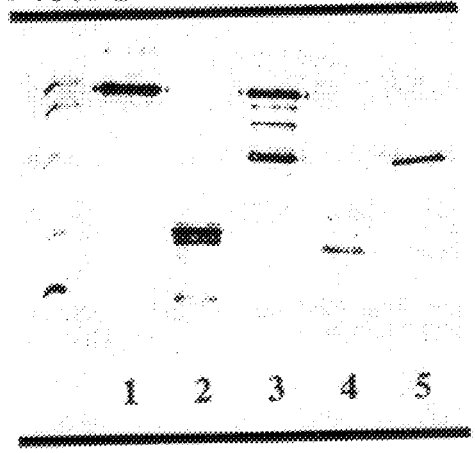
FIG. 9D 4-week

FIG.11A

Comparison of Hin47

```
MKKTRFVLNSIALGLSVLSTSFVAQATLPSFVSEQNSLAPMLEKVQPAVV      SB33
................M.....................................  SB12

TLSVEGKAKVDSRSPFLDDIPEEFKFFFGDRFAEQFGGRGESKRNFRGLG       SB33
.................................................       SB12

SGVIINASKGYVLTNNHVIDEADKITVQLQDGREFKAKLVGKDELSDIAL       SB33
.................G......................Q........       SB12

VQLEKPSNLTEIKFADSDKLRVGDFTVAIGNPFGLGQTVTSGIVSALGRS       SB33
..................................................      SB12

TGSDSGTYENYIQTDAAVNRGNSGGALVNLNGELIGINTAIISPSGGNAG       SB33
..................................................      SB12
```

FIG.11B

```
IAFAIPSNQASNLVQQILEFGQVRRGLLGIKGGELNADLAKAFNVSAQQG      SB33
..................C..........................        SB12

AFVSEVLPKSAAEKAGLKAGDIITAMNGQKISSFAEIRAKIATTGAGKEI      SB33
.................G...............................    SB12

SLTYLRDGKSHDVKMKLQADDSSQLSSKTELPALDGATLKDYDAKGVKGI      SB33
..........G.......................................    SB12

EITKIQPNSLAAQRGLKSGDIIIGINRQMIENIRELNKVLETEPSAVALN      SB33
............................................K....    SB12

ILRGDSNFYLLVQ*                                         SB33
.....N......**                                         SB12
```

Purification of Hin47 Mutant H91A From *E. coli*

1. *E. coli* Whole cells
2. Soluble proteins after 50 mM Tris, pH 8, extraction
3. Flow-through fraction after DEAE Sephacel column
4. Purified H91A from hydroxyapatite column

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2894 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGATCCGTTA   ATACTGAAAT   AAATGGCACA   CCTTTTTCAC   GCATTTGGGC   AAGTACAGCA     60
CTGGTTTTTG   CCATTTGCAT   TAAAGAGAAT   AATGCTTCCT   GCATACGAGC   ACCACCACTC    120
GCAGAGAAAC   ATACAAACGG   ACAATTCATT   TCCATCGCTT   TTTCAGCCGC   TTTAACAAAT    180
TTTGCACCAA   CTACAGAACC   CATTGAACCG   CCCATAAAAG   CAAAGTTCGA   TGCAGCCACA    240
ACAATTGGCA   TATCATAAAG   TGTACCTGTC   ATAGTAATTA   GCGCATCTTT   CTCGCCCGTT    300
TCTTTTTGTG   CCGCATTGAT   ACGATCTTTA   TATTTCTTTA   AATCTTTAAA   TTTTAAAATA    360
TCTTTTGGTT   CTAAATCTGC   CGCAATTTCT   TGGCTTGAAT   CTTCGTCCAA   TAAATTTAAT    420
AAACGCTCAC   GAGCATCAAT   ACGCATATGA   TGACCACATT   TCGGGCAAAC   ATACAGATTA    480
CGTTTGAGTT   CTTCACTATA   AAGTACTTGT   TCACAAGCAG   TACATTTGT    CCATACGCCT    540
TCTGGCACAT   TGGCTTTTCG   AGTGGAAGAA   GAAGGACTTT   TACTAAAAAT   TCGGTTAATC    600
CAGCTCATTT   TTTGACCTTT   TTATTGACTA   GAAAATTGCG   CGTATTAGAA   CATAAATTTA    660
TAGAATTTGC   TACTTGTAAG   ACCGTTTTTG   TACTGCTCCG   ATTTCCTTTT   AAACAAGATA    720
ATTTGCTCTC   CTCTTATTGA   ACATTTTTTT   TATTTTTTTG   TCTTACTGAC   CACGTTATCT    780
GAAATTTATT   TTGGAGTATT   TATGAAAAAA   ACACGTTTTG   TACTAAATAG   TATTGCACTT    840
GGATTAAGTG   TATTAAGCAC   ATCATTTGTT   GCTCAAGCCA   CTTTGCCAAG   TTTTGTTTCG    900
GAACAAAACA   GTCTTGCACC   AATGTTAGAA   AAAGTACAAC   CTGCCGTTGT   CACTCTTTCC    960
GTTGAAGGAA   AAGCTAAAGT   AGATTCTCGT   TCTCCTTTCC   TAGACGATAT   TCCTGAAGAA   1020
TTTAAATTCT   TCTTTGGCGA   TCGTTTTGCC   GAACAATTTG   GTGGACGTGG   AGAATCAAAG   1080
CGTAACTTCC   GTGGTTTAGG   TTCTGGTGTC   ATTATTAATG   CAAGCAAAGG   CTATGTTTTA   1140
ACCAATAATC   ATGTTATTGA   TGAAGCTGAT   AAAATTACCG   TGCAATTACA   AGATGGGCGT   1200
GAATTTAAAG   CAAAATTAGT   GGGTAAAGAT   GAACTATCAG   ATATTGCATT   AGTACAGCTT   1260
GAAAAACCAA   GTAATTTAAC   AGAAATCAAA   TTTGCTGATT   CCGACAAATT   ACGCGTAGGC   1320
GATTTCACTG   TTGCAATCGG   TAATCCATTT   GGTTTAGGTC   AAACTGTGAC   ATCAGGTATT   1380
GTTTCTGCAT   TGGGTCGTTC   AACAGGTTCT   GACAGTGGCA   CTTATGAAAA   CTATATTCAA   1440
```

| | | | | |
|---|---|---|---|---|
| ACCGATGCAG | CAGTAAACCG | CGGTAATTCG | GGTGGAGCGT | TAGTAAACTT | AAATGGCGAA | 1500 |
| CTTATTGGAA | TTAATACCGC | AATTATTTCT | CCAAGCGGTG | GCAATGCAGG | AATTGCCTTT | 1560 |
| GCGATTCCAA | GTAATCAAGC | AAGCAATTTA | GTGCAACAAA | TTTTAGAATT | TGGTCAAGTG | 1620 |
| CGTCGCGGAT | TGCTTGGTAT | TAAAGGTGGC | GAACTCAATG | CTGATTTAGC | CAAAGCCTTT | 1680 |
| AATGTAAGCG | CGCAACAAGG | CGCATTTGTA | AGTGAAGTTT | TACCGAAATC | TGCTGCTGAA | 1740 |
| AAAGCAGGAC | TTAAAGCGGG | CGATATTATC | ACGGCGATGA | ACGGTCAAAA | AATCTCAAGT | 1800 |
| TTCGCTGAAA | TTCGTGCAAA | AATCGCAACC | ACTGGTGCAG | GCAAAGAGAT | TAGCTTGACT | 1860 |
| TACTTACGTG | ATGGCAAATC | CCACGACGTT | AAAATGAAAT | TACAAGCGGA | TGATAGTAGC | 1920 |
| CAACTTTCCT | CAAAAACTGA | GTTGCCTGCA | TTAGATGGTG | CAACATTGAA | AGACTACGAT | 1980 |
| GCTAAAGGCG | TTAAAGGAAT | TGAAATCACA | AAAATTCAAC | CTAATTCGCT | GGCTGCACAA | 2040 |
| CGTGGTTTAA | AATCGGGCGA | TATTATTATT | GGTATTAATC | GTCAAATGAT | CGAAAACATT | 2100 |
| CGTGAATTAA | ATAAAGTGCT | TGAAACTGAA | CCGTCAGCAG | TTGCACTTAA | TATTTTACGA | 2160 |
| GGTGACAGTA | ATTTCTATTT | ATTAGTGCAA | TAATCTGCTT | GATATATTTA | AGAAAAAAGT | 2220 |
| CCGATCACAA | TGATCGGGCT | TCTTTTTATG | CAGCAATCGT | TCTTAACAAA | TCCACCACAA | 2280 |
| ATTCTAACCG | CACTTTGTTA | TCAGATAAAT | CTTTCATGAA | CTTAAATTTT | AATGGGCCAT | 2340 |
| CAAATCGATA | CACAATAGGT | TCTTTTTGAA | TTAATTGAAT | AAATTTATCT | GGATTCACTT | 2400 |
| GTGCTTTTGC | TGAAAACTCA | ATAAAACCGC | CTTGTGTTCC | TGCATCAATT | CGCACAACTT | 2460 |
| TCAACGGCTC | AACCAACAAA | CGCAATTCTG | CAATTTGCAG | TAAATTTTTT | GTTGCATCAG | 2520 |
| GCAATAATCC | GAATCGATCT | ATTAACTCAA | CTTTTAATTC | ATCTAATTCT | GCTTACTCT | 2580 |
| CTGCTGCAGC | AATGCGTTTA | TAAAAGGATA | AACGCATATT | CACGTCTCCT | AGATAATCAT | 2640 |
| CAGGCAGTAA | AGCAGGCACA | CGCAATTCAA | TATCCGCTTG | TTGTTGCGTC | AATTCTTCTA | 2700 |
| ATGATGGTTC | ACGCCCTTCT | TTTAACGCTT | TAACCGCTGC | ATCCAATAAT | TCCATATAAA | 2760 |
| GCGAAAAACC | GATGCTTTCA | ATTTGTCCAC | TTTGTTCGTT | TCCAAGTAAT | TCGCCGGCAC | 2820 |
| CACGAATCTC | TAAATCGTGG | GTTGCCAAGA | TAAAACCAGC | CCAAGATTA | TCAAGATTTT | 2880 |
| CCAAGGCATC | TAGA | | | | | 2894 |

( 2 ) INFORMATION FOR SEQ ID NO:2:

( i ) SEQUENCE CHARACTERISTICS:
        ( A ) LENGTH: 463 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Met Lys Lys Thr Arg Phe Val Leu Asn Ser Ile Ala Leu Gly Leu Ser
 1               5                  10                  15

Val Leu Ser Thr Ser Phe Val Ala Gln Ala Thr Leu Pro Ser Phe Val
             20                  25                  30

Ser Glu Gln Asn Ser Leu Ala Pro Met Leu Glu Lys Val Gln Pro Ala
         35                  40                  45

Val Val Thr Leu Ser Val Glu Gly Lys Ala Lys Val Asp Ser Arg Ser
     50                  55                  60

Pro Phe Leu Asp Asp Ile Pro Glu Glu Phe Lys Phe Phe Phe Gly Asp
65                   70                  75                  80

Arg Phe Ala Glu Gln Phe Gly Gly Arg Gly Glu Ser Lys Arg Asn Phe
                 85                  90                  95

Arg Gly Leu Gly Ser Gly Val Ile Ile Asn Ala Ser Lys Gly Tyr Val
```

|     |     |     |     |     | 100 |     |     |     |     | 105 |     |     |     |     | 110 |     |
| --- | --- | --- | --- | --- | --- | --- | --- | --- | --- | --- | --- | --- | --- | --- | --- | --- |
| Leu | Thr | Asn<br>115 | Asn | His | Val | Ile | Asp<br>120 | Glu | Ala | Asp | Lys | Ile<br>125 | Thr | Val | Gln |
| Leu | Gln<br>130 | Asp | Gly | Arg | Glu | Phe<br>135 | Lys | Ala | Lys | Leu | Val<br>140 | Gly | Lys | Asp | Glu |
| Leu<br>145 | Ser | Asp | Ile | Ala | Leu<br>150 | Val | Gln | Leu | Glu | Lys<br>155 | Pro | Ser | Asn | Leu | Thr<br>160 |
| Glu | Ile | Lys | Phe | Ala<br>165 | Asp | Ser | Asp | Lys | Leu<br>170 | Arg | Val | Gly | Asp | Phe<br>175 | Thr |
| Val | Ala | Ile | Gly<br>180 | Asn | Pro | Phe | Gly | Leu<br>185 | Gly | Gln | Thr | Val | Thr<br>190 | Ser | Gly |
| Ile | Val | Ser<br>195 | Ala | Leu | Gly | Arg | Ser<br>200 | Thr | Gly | Ser | Asp | Ser<br>205 | Gly | Thr | Tyr |
| Glu | Asn<br>210 | Tyr | Ile | Gln | Thr | Asp<br>215 | Ala | Ala | Val | Asn | Arg<br>220 | Gly | Asn | Ser | Gly |
| Gly<br>225 | Ala | Leu | Val | Asn | Leu<br>230 | Asn | Gly | Glu | Leu | Ile<br>235 | Gly | Ile | Asn | Thr | Ala<br>240 |
| Ile | Ile | Ser | Pro | Ser<br>245 | Gly | Gly | Asn | Ala | Gly<br>250 | Ile | Ala | Phe | Ala | Ile<br>255 | Pro |
| Ser | Asn | Gln | Ala<br>260 | Ser | Asn | Leu | Val | Gln<br>265 | Gln | Ile | Leu | Glu | Phe<br>270 | Gly | Gln |
| Val | Arg | Arg<br>275 | Gly | Leu | Leu | Gly | Ile<br>280 | Lys | Gly | Gly | Glu | Leu<br>285 | Asn | Ala | Asp |
| Leu | Ala<br>290 | Lys | Ala | Phe | Asn | Val<br>295 | Ser | Ala | Gln | Gln | Gly<br>300 | Ala | Phe | Val | Ser |
| Glu<br>305 | Val | Leu | Pro | Lys | Ser<br>310 | Ala | Ala | Glu | Lys | Ala<br>315 | Gly | Leu | Lys | Ala | Gly<br>320 |
| Asp | Ile | Ile | Thr | Ala<br>325 | Met | Asn | Gly | Gln | Lys<br>330 | Ile | Ser | Ser | Phe | Ala<br>335 | Glu |
| Ile | Arg | Ala | Lys<br>340 | Ile | Ala | Thr | Thr | Gly<br>345 | Ala | Gly | Lys | Glu | Ile<br>350 | Ser | Leu |
| Thr | Tyr | Leu<br>355 | Arg | Asp | Gly | Lys | Ser<br>360 | His | Asp | Val | Lys | Met<br>365 | Lys | Leu | Gln |
| Ala | Asp<br>370 | Asp | Ser | Ser | Gln | Leu<br>375 | Ser | Ser | Lys | Thr | Glu<br>380 | Leu | Pro | Ala | Leu |
| Asp<br>385 | Gly | Ala | Thr | Leu | Lys<br>390 | Asp | Tyr | Asp | Ala | Lys<br>395 | Gly | Val | Lys | Gly | Ile<br>400 |
| Glu | Ile | Thr | Lys | Ile<br>405 | Gln | Pro | Asn | Ser | Leu<br>410 | Ala | Ala | Gln | Arg | Gly<br>415 | Leu |
| Lys | Ser | Gly | Asp<br>420 | Ile | Ile | Ile | Gly | Ile<br>425 | Asn | Arg | Gln | Met | Ile<br>430 | Glu | Asn |
| Ile | Arg | Glu<br>435 | Leu | Asn | Lys | Val | Leu<br>440 | Glu | Thr | Glu | Pro | Ser<br>445 | Ala | Val | Ala |
| Leu | Asn<br>450 | Ile | Leu | Arg | Gly | Asp<br>455 | Ser | Asn | Phe | Tyr | Leu<br>460 | Leu | Val | Gln |     |

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATGAAAAAAA CACGTTTTGT ATTAAATAGT ATTGCACTTG G        41

(2) INFORMATION FOR SEQ ID NO:4:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO:4:

```
Met Lys Lys Thr Arg Phe Val Leu Asn Ser Ile Ala Leu Gly Leu Ser
 1           5                  10                  15
Val Leu Ser Thr Ser Phe Val Ala Gln Ala Thr Leu Pro Ser Phe Val
             20                  25                  30
Ser Glu Gln Asn Ser
         35
```

(2) INFORMATION FOR SEQ ID NO:5:

(i) SEQUENCE CHARACTERISTICS:
        (A) LENGTH: 472 amino acids
        (B) TYPE: amino acid
        (C) STRANDEDNESS: single
        (D) TOPOLOGY: linear (xi) SEQUENCE DESCRIPTION: SEQ ID NO:5:

```
Met Lys Lys Thr Thr Leu Ala Leu Ser Arg Leu Ala Leu Ser Leu Ser
 1           5                  10                  15
Leu Ala Leu Ser Pro Leu Ser Ala Thr Ala Ala Glu Thr Ser Ser Ala
             20                  25                  30
Thr Thr Ala Gln Gln Met Pro Ser Leu Ala Pro Met Leu Glu Lys Val
             35                  40                  45
Met Pro Ser Val Val Ser Ile Asn Val Glu Gly Ser Thr Thr Val Asn
 50                  55                  60
Thr Pro Arg Met Pro Arg Asn Phe Gln Gln Phe Phe Gly Asp Asp Ser
 65                  70                  75                  80
Pro Phe Cys Gln Glu Gly Ser Pro Phe Gln Ser Ser Pro Phe Cys Gln
                     85                  90                  95
Gly Gly Gln Gly Gly Asn Gly Gly Gly Gln Gln Gln Lys Phe Met Ala
                 100                 105                 110
Leu Gly Ser Gly Val Ile Ile Asp Ala Asp Lys Gly Tyr Val Val Thr
             115                 120                 125
Asn Asn His Val Val Asp Asn Ala Thr Val Ile Lys Val Gln Leu Ser
         130                 135                 140
Asp Gly Arg Lys Phe Asp Ala Lys Met Val Gly Lys Asp Pro Arg Ser
145                 150                 155                 160
Asp Ile Ala Leu Ile Gln Ile Gln Asn Pro Lys Asn Leu Thr Ala Ile
                 165                 170                 175
Lys Met Ala Asp Ser Asp Ala Leu Arg Val Gly Asp Tyr Thr Val Gly
             180                 185                 190
Ile Gly Asn Pro Phe Gly Leu Gly Glu Thr Val Thr Ser Gly Ile Val
         195                 200                 205
Ser Ala Leu Gly Arg Ser Gly Leu Asn Ala Glu Asn Tyr Glu Asn Phe
     210                 215                 220
Ile Gln Thr Asp Ala Ala Ile Asn Arg Gly Asn Ser Gly Gly Ala Leu
225                 230                 235                 240
Val Asn Leu Asn Gly Glu Leu Ile Gly Ile Asn Thr Ala Ile Leu Ala
                 245                 250                 255
```

```
Pro  Asp  Gly  Gly  Asn  Ile  Gly  Ile  Gly  Phe  Ala  Ile  Pro  Ser  Asn  Met
               260                 265                     270

Val  Lys  Asn  Leu  Thr  Ser  Gln  Met  Val  Glu  Tyr  Gly  Gln  Val  Lys  Arg
          275                 280                     285

Gly  Glu  Leu  Gly  Ile  Met  Gly  Thr  Glu  Leu  Asn  Ser  Glu  Leu  Ala  Lys
     290                      295                     300

Ala  Met  Lys  Val  Asp  Ala  Gln  Arg  Gly  Ala  Phe  Val  Ser  Gln  Val  Leu
305                      310                     315                          320

Pro  Asn  Ser  Ser  Ala  Ala  Lys  Ala  Gly  Ile  Lys  Ala  Gly  Asp  Val  Ile
                    325                      330                     335

Thr  Ser  Leu  Asn  Gly  Lys  Pro  Ile  Ser  Ser  Phe  Ala  Ala  Leu  Arg  Ala
               340                 345                          350

Gln  Val  Gly  Thr  Met  Pro  Val  Gly  Ser  Lys  Leu  Thr  Leu  Gly  Leu  Leu
          355                      360                     365

Arg  Asp  Gly  Lys  Gln  Val  Asn  Val  Asn  Leu  Glu  Leu  Gln  Gln  Ser  Ser
     370                      375                     380

Gln  Asn  Gln  Val  Asp  Ser  Ser  Ile  Phe  Asn  Gly  Ile  Glu  Gly  Ala
385                      390                      395                     400

Glu  Met  Ser  Asn  Lys  Gly  Lys  Asp  Gln  Gly  Val  Val  Val  Asn  Asn  Val
                    405                      410                     415

Lys  Thr  Gly  Thr  Pro  Ala  Ala  Gln  Ile  Gly  Leu  Lys  Lys  Gly  Asp  Val
               420                      425                     430

Ile  Ile  Gly  Ala  Asn  Gln  Ile  Ala  Val  Lys  Asn  Ile  Ala  Glu  Ile  Arg
          435                      440                     445

Lys  Val  Leu  Asp  Ser  Lys  Pro  Ser  Val  Leu  Ala  Leu  Asn  Ile  Gln  Arg
     450                      455                     460

Gly  Asp  Arg  His  Leu  Pro  Val  Asn
465                      470
```

( 2 ) INFORMATION FOR SEQ ID NO:6:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Met  Lys  Lys  Thr  Thr  Leu  Ala  Met  Ser  Ala  Leu  Ala  Leu  Ser  Leu  Gly
1                   5                    10                      15

Leu  Ala  Leu  Ser  Pro  Leu  Ser  Ala  Thr  Ala  Ala  Glu  Thr  Ser  Ser  Ser
               20                       25                      30

Ala  Met  Thr  Ala  Gln  Gln  Met  Pro  Ser  Leu  Ala  Pro  Met  Leu  Glu  Lys
          35                       40                      45

Val  Met  Pro  Ser  Val  Val  Ser  Ile  Asn  Val  Glu  Gly  Ser  Thr  Thr  Val
     50                       55                      60

Asn  Thr  Pro  Arg  Met  Pro  Arg  Asn  Phe  Gln  Gln  Phe  Phe  Gly  Asp  Asp
65                       70                      75                           80

Ser  Pro  Phe  Cys  Gln  Asp  Gly  Ser  Pro  Phe  Gln  Asn  Ser  Pro  Phe  Cys
                    85                       90                          95

Gln  Gly  Gly  Gly  Asn  Gly  Gly  Asn  Gly  Gly  Gln  Gln  Gln  Lys  Phe  Met
                    100                      105                     110

Ala  Leu  Gly  Ser  Gly  Val  Ile  Ile  Asp  Ala  Asp  Lys  Gly  Tyr  Val  Val
          115                      120                     125

Thr  Asn  Asn  His  Val  Val  Asp  Asn  Ala  Ser  Val  Ile  Lys  Val  Gln  Leu
     130                      135                     140
```

```
Ser  Asp  Gly  Arg  Lys  Phe  Asp  Ala  Lys  Val  Val  Gly  Lys  Asp  Pro  Arg
145                 150                      155                      160

Ser  Asp  Ile  Ala  Leu  Ile  Gln  Ile  Gln  Asn  Pro  Lys  Asn  Leu  Thr  Ala
                    165                      170                      175

Ile  Lys  Leu  Ala  Asp  Ser  Asp  Ala  Leu  Arg  Val  Gly  Asp  Tyr  Thr  Val
                    180                      185                      190

Ala  Ile  Gly  Asn  Pro  Phe  Gly  Leu  Gly  Glu  Thr  Val  Thr  Ser  Gly  Ile
               195                      200                      205

Val  Ser  Ala  Leu  Gly  Arg  Ser  Gly  Leu  Asn  Val  Glu  Asn  Tyr  Glu  Asn
          210                      215                      220

Phe  Ile  Gln  Thr  Asp  Ala  Ala  Ile  Asn  Arg  Gly  Asn  Ser  Gly  Gly  Ala
225                           230                      235                      240

Leu  Val  Asn  Leu  Asn  Gly  Glu  Leu  Ile  Gly  Ile  Asn  Thr  Ala  Ile  Leu
                    245                      250                      255

Ala  Pro  Asp  Gly  Gly  Asn  Ile  Gly  Ile  Gly  Phe  Ala  Ile  Pro  Ser  Asn
               260                      265                      270

Met  Val  Lys  Asn  Leu  Thr  Ser  Gln  Met  Val  Glu  Tyr  Gly  Gln  Val  Arg
               275                      280                      285

Arg  Gly  Glu  Leu  Gly  Ile  Met  Gly  Thr  Glu  Leu  Asn  Ser  Glu  Leu  Ala
     290                      295                      300

Lys  Ala  Met  Lys  Val  Asp  Ala  Gln  Arg  Gly  Ala  Phe  Val  Ser  Gln  Val
305                      310                      315                      320

Met  Pro  Asn  Ser  Ser  Ala  Ala  Lys  Ala  Gly  Ile  Lys  Ala  Gly  Asp  Val
                    325                      330                      335

Ile  Thr  Ser  Leu  Asn  Gly  Lys  Pro  Ile  Ser  Ser  Phe  Ala  Ala  Leu  Arg
                    340                      345                      350

Ala  Gln  Val  Gly  Thr  Met  Pro  Val  Gly  Ser  Lys  Ile  Ser  Leu  Gly  Leu
               355                      360                      365

Leu  Arg  Glu  Gly  Lys  Ala  Ile  Thr  Val  Asn  Leu  Glu  Leu  Gln  Gln  Ser
     370                      375                      380

Ser  Gln  Ser  Gln  Val  Asp  Ser  Ser  Thr  Ile  Phe  Ser  Gly  Ile  Glu  Gly
385                      390                      395                      400

Ala  Glu  Met  Ser  Asn  Lys  Gly  Gln  Asp  Lys  Gly  Val  Val  Val  Ser  Ser
               405                      410                      415

Val  Lys  Ala  Asn  Ser  Pro  Ala  Ala  Gln  Ile  Gly  Leu  Lys  Lys  Gly  Asp
               420                      425                      430

Val  Ile  Ile  Gly  Ala  Asn  Gln  Ile  Pro  Val  Lys  Asn  Ile  Ala  Glu  Ile
          435                      440                      445

Arg  Lys  Ile  Leu  Asp  Ser  Lys  Pro  Ser  Val  Leu  Ala  Leu  Asn  Ile  Gln
     450                      455                      460

Arg  Gly  Asp  Ser  Ser  Ile  Tyr  Leu  Leu  Met  Gln
465                      470                      475
```

(2) INFORMATION FOR SEQ ID NO:7:

(i) SEQUENCE CHARACTERISTICS:
        (A) LENGTH: 228 amino acids
        (B) TYPE: amino acid
        (C) STRANDEDNESS: single
        (D) TOPOLOGY: linear (xi) SEQUENCE DESCRIPTION: SEQ ID NO:7:

```
Ile  Val  Gly  Gly  Tyr  Lys  Cys  Glu  Lys  Asn  Ser  Gln  Pro  Trp  Gln  Val
1                   5                        10                       15

Ala  Val  Ile  Asn  Glu  Tyr  Leu  Cys  Gly  Gly  Val  Leu  Ile  Asp  Pro  Ser
               20                       25                       30
```

| | | | | | | | | | | | | | | |
|---|---|---|---|---|---|---|---|---|---|---|---|---|---|---|
|Trp|Val|Ile<br>35|Thr|Ala|Ala|His|Cys<br>40|Tyr|Ser|Asn|Asn|Tyr<br>45|Gln|Val|Leu|

| | | | | | | | | | | | | | | |
|---|---|---|---|---|---|---|---|---|---|---|---|---|---|---|
|Leu|Gly<br>50|Arg|Asn|Asn|Leu|Phe<br>55|Lys|Asp|Glu|Pro|Phe<br>60|Ala|Gln|Arg|Arg|

| | | | | | | | | | | | | | | |
|---|---|---|---|---|---|---|---|---|---|---|---|---|---|---|
|Leu<br>65|Val|Pro|Gln|Ser|Phe<br>70|Arg|His|Pro|Asp|Tyr<br>75|Ile|Pro|Leu|Ile|Pro<br>80|

| | | | | | | | | | | | | | | |
|---|---|---|---|---|---|---|---|---|---|---|---|---|---|---|
|Val|His|Asp|His|Ser<br>85|Asn|Asp|Leu|Met|Leu<br>90|Leu|His|Leu|Ser|Glu<br>95|Pro|

| | | | | | | | | | | | | | | |
|---|---|---|---|---|---|---|---|---|---|---|---|---|---|---|
|Ala|Asp|Ile|Thr<br>100|Gly|Gly|Val|Lys|Val<br>105|Ile|Asp|Leu|Pro|Thr<br>110|Lys|Glu|

| | | | | | | | | | | | | | | |
|---|---|---|---|---|---|---|---|---|---|---|---|---|---|---|
|Pro|Lys|Val<br>115|Gly|Ser|Thr|Cys|Leu<br>120|Ala|Ser|Gly|Trp|Gly<br>125|Ser|Thr|Asn|

| | | | | | | | | | | | | | | |
|---|---|---|---|---|---|---|---|---|---|---|---|---|---|---|
|Pro|Ser|Glu<br>130|Met|Val|Val|Ser|His<br>135|Asp|Leu|Gln|Cys|Val<br>140|Asn|Ile|His|

| | | | | | | | | | | | | | | |
|---|---|---|---|---|---|---|---|---|---|---|---|---|---|---|
|Leu|Leu|Ser|Asn|Glu<br>150|Lys|Cys|Ile|Glu|Thr|Tyr<br>155|Lys|Asp|Asn|Val|Thr<br>160|

(Leu 145 begins row)

| | | | | | | | | | | | | | | |
|---|---|---|---|---|---|---|---|---|---|---|---|---|---|---|
|Asp|Val|Met|Leu|Cys<br>165|Ala|Gly|Glu|Met|Glu<br>170|Gly|Gly|Lys|Asp|Thr<br>175|Cys|

| | | | | | | | | | | | | | | |
|---|---|---|---|---|---|---|---|---|---|---|---|---|---|---|
|Ala|Gly|Asp|Ser<br>180|Gly|Gly|Pro|Leu|Ile<br>185|Cys|Asp|Gly|Val|Leu<br>190|Gln|Gly|

| | | | | | | | | | | | | | | |
|---|---|---|---|---|---|---|---|---|---|---|---|---|---|---|
|Ile|Thr|Ser<br>195|Gly|Gly|Ala|Thr|Pro<br>200|Cys|Ala|Lys|Pro|Lys<br>205|Thr|Pro|Ala|

| | | | | | | | | | | | | | | |
|---|---|---|---|---|---|---|---|---|---|---|---|---|---|---|
|Ile|Tyr<br>210|Ala|Lys|Leu|Ile|Lys<br>215|Phe|Thr|Ser|Trp|Ile<br>220|Lys|Lys|Val|Met|

| | | |
|---|---|---|
|Lys<br>225|Glu|Asn|Pro|

(2) INFORMATION FOR SEQ ID NO:8:

(i) SEQUENCE CHARACTERISTICS:
    (A) LENGTH: 232 amino acids
    (B) TYPE: amino acid
    (C) STRANDEDNESS: single
    (D) TOPOLOGY: linear (xi) SEQUENCE DESCRIPTION: SEQ ID NO:8:

| | | | | | | | | | | | | | | |
|---|---|---|---|---|---|---|---|---|---|---|---|---|---|---|
|Ile<br>1|Ile|Gly|Gly|Arg<br>5|Glu|Cys|Glu|Lys|Asn<br>10|Ser|His|Pro|Trp|Gln<br>15|Val|

| | | | | | | | | | | | | | | |
|---|---|---|---|---|---|---|---|---|---|---|---|---|---|---|
|Ala|Ile|Tyr|His<br>20|Tyr|Ser|Ser|Phe|Gln<br>25|Cys|Gly|Gly|Val|Leu<br>30|Val|Asn|

| | | | | | | | | | | | | | | |
|---|---|---|---|---|---|---|---|---|---|---|---|---|---|---|
|Pro|Lys|Trp|Val<br>35|Leu|Thr|Ala|Ala|His<br>40|Cys|Lys|Asn|Asp|Asn<br>45|Tyr|Glu|

| | | | | | | | | | | | | | | |
|---|---|---|---|---|---|---|---|---|---|---|---|---|---|---|
|Val|Trp|Leu|Gly<br>50|Arg|His|Asn|Leu|Phe<br>55|Glu|Asn|Glu|Asn|Thr<br>60|Ala|Gln|

| | | | | | | | | | | | | | | |
|---|---|---|---|---|---|---|---|---|---|---|---|---|---|---|
|Phe<br>65|Phe|Gly|Val|Thr|Ala<br>70|Asp|Phe|Pro|His|Pro<br>75|Gly|Phe|Asn|Leu|Ser<br>80|

| | | | | | | | | | | | | | | |
|---|---|---|---|---|---|---|---|---|---|---|---|---|---|---|
|Ala|Asp|Gly|Lys|Asp<br>85|Tyr|Ser|His|Asp|Leu<br>90|Met|Leu|Leu|Arg|Leu<br>95|Gln|

| | | | | | | | | | | | | | | |
|---|---|---|---|---|---|---|---|---|---|---|---|---|---|---|
|Ser|Pro|Ala|Lys<br>100|Ile|Thr|Asp|Ala|Val<br>105|Lys|Val|Leu|Glu|Leu<br>110|Pro|Thr|

| | | | | | | | | | | | | | | |
|---|---|---|---|---|---|---|---|---|---|---|---|---|---|---|
|Gln|Glu|Pro<br>115|Glu|Leu|Gly|Ser|Thr<br>120|Cys|Glu|Ala|Ser|Gly<br>125|Trp|Gly|Ser|

| | | | | | | | | | | | | | | |
|---|---|---|---|---|---|---|---|---|---|---|---|---|---|---|
|Ile|Glu<br>130|Pro|Gly|Pro|Asp|Asp<br>135|Phe|Glu|Phe|Pro|Asp<br>140|Glu|Ile|Gln|Cys|

| | | | | | | | | | | | | | | |
|---|---|---|---|---|---|---|---|---|---|---|---|---|---|---|
|Val<br>145|Gln|Leu|Thr|Leu|Leu<br>150|Gln|Asn|Thr|Phe|Cys<br>155|Ala|Asp|Ala|His|Pro<br>160|

-continued

```
Asp Lys Val Thr Glu Ser Met Leu Cys Ala Gly Tyr Leu Pro Gly Gly
            165                 170                 175

Lys Asp Thr Cys Met Gly Asp Ser Gly Gly Pro Leu Ile Cys Asn Gly
            180                 185                 190

Met Trp Gln Gly Ile Thr Ser Trp Gly His Thr Pro Cys Gly Ser Ala
            195                 200                 205

Asn Lys Pro Ser Ile Tyr Thr Lys Leu Ile Phe Tyr Leu Asp Trp Ile
210                 215                 220

Asp Asp Thr Ile Thr Glu Asn Pro
225                 230
```

( 2 ) INFORMATION FOR SEQ ID NO:9:

( i ) SEQUENCE CHARACTERISTICS:
        ( A ) LENGTH: 223 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Ile Val Gly Gly Tyr Thr Cys Gly Ala Asn Thr Val Pro Tyr Gln Val
1               5                   10                  15

Ser Leu Asn Ser Gly Tyr His Phe Cys Gly Gly Ser Leu Ile Asn Ser
                20                  25                  30

Gln Trp Val Val Ser Ala Ala His Cys Tyr Lys Ser Gly Ile Gln Val
            35                  40                  45

Arg Leu Gly Glu Asp Asn Ile Asn Val Val Glu Gly Asn Glu Gln Phe
    50                  55                  60

Ile Ser Ala Ser Lys Ser Ile Val His Pro Ser Tyr Asn Ser Asn Thr
65                  70                  75                  80

Leu Asn Asn Asp Ile Met Leu Ile Lys Leu Lys Ser Ala Ala Ser Leu
                85                  90                  95

Asn Ser Arg Val Ala Ser Ile Ser Leu Pro Thr Ser Cys Ala Ser Ala
            100                 105                 110

Gly Thr Gln Cys Leu Ile Ser Gly Trp Gly Asn Thr Lys Ser Ser Gly
        115                 120                 125

Thr Ser Tyr Pro Asp Val Leu Lys Cys Leu Lys Ala Pro Ile Leu Ser
    130                 135                 140

Asp Ser Ser Cys Lys Ser Ala Tyr Pro Gly Gln Ile Thr Ser Asn Met
145                 150                 155                 160

Phe Cys Ala Gly Tyr Leu Glu Gly Gly Lys Asp Ser Cys Gln Gly Asp
                165                 170                 175

Ser Gly Gly Pro Val Val Cys Ser Gly Lys Leu Gln Gly Ile Val Ser
            180                 185                 190

Trp Gly Ser Gly Cys Ala Gln Lys Asn Lys Pro Gly Val Tyr Thr Lys
        195                 200                 205

Val Cys Asn Tyr Val Ser Trp Ile Lys Gln Thr Ile Ala Ser Asn
    210                 215                 220
```

( 2 ) INFORMATION FOR SEQ ID NO:10:

( i ) SEQUENCE CHARACTERISTICS:
        ( A ) LENGTH: 228 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Ile Val Asn Gly Glu Glu Ala Val Pro Gly Ser Trp Pro Trp Gln Val
```

|   |   |   |   | 1 |   |   |   |   | 5 |   |   |   |   | 10 |   |   |   |   | 15 |
|---|---|---|---|---|---|---|---|---|---|---|---|---|---|---|---|---|---|---|---|
| Ser | Leu | Gln | Asp 20 | Lys | Thr | Gly | Phe | His 25 | Phe | Cys | Gly | Gly | Ser 30 | Leu | Ile |
| Asn | Glu | Asn 35 | Trp | Val | Val | Thr | Ala 40 | Ala | His | Cys | Gly | Val 45 | Thr | Thr | Ser |
| Asp | Val 50 | Val | Val | Ala | Gly | Glu 55 | Phe | Asp | Gln | Gly | Ser 60 | Ser | Ser | Glu | Lys |
| Ile 65 | Gln | Lys | Leu | Lys | Ile 70 | Ala | Lys | Val | Phe | Lys 75 | Asn | Ser | Lys | Tyr | Asn 80 |
| Ser | Leu | Thr | Ile | Asn 85 | Asn | Asp | Ile | Thr | Leu 90 | Leu | Lys | Leu | Ser | Thr 95 | Ala |
| Ala | Ser | Phe | Ser 100 | Gln | Thr | Val | Ser | Ala 105 | Val | Cys | Leu | Pro | Ser 110 | Ala | Ser |
| Asp | Asp | Phe 115 | Ala | Ala | Gly | Thr | Thr 120 | Cys | Val | Thr | Thr | Gly 125 | Trp | Gly | Leu |
| Thr | Arg 130 | Tyr | Ala | Asn | Thr | Pro 135 | Asp | Arg | Leu | Gln | Gln 140 | Ala | Ser | Leu | Pro |
| Leu 145 | Leu | Ser | Asn | Thr | Asn 150 | Cys | Lys | Lys | Tyr | Trp 155 | Gly | Thr | Lys | Ile | Lys 160 |
| Asp | Ala | Met | Ile | Cys 165 | Ala | Gly | Ala | Ser | Gly 170 | Val | Ser | Ser | Cys | Met 175 | Gly |
| Asp | Ser | Gly | Gly 180 | Pro | Leu | Val | Cys | Lys 185 | Lys | Asn | Gly | Ala | Trp 190 | Thr | Leu |
| Val | Gly | Ile 195 | Val | Ser | Trp | Gly | Ser 200 | Ser | Thr | Cys | Ser | Thr 205 | Ser | Thr | Pro |
| Gly | Val 210 | Tyr | Ala | Arg | Val | Thr 215 | Ala | Leu | Val | Asn | Trp 220 | Val | Gln | Gln | Thr |
| Leu 225 | Ala | Ala | Asn |   |   |   |   |   |   |   |   |   |   |   |   |

(2) INFORMATION FOR SEQ ID NO:11:

(i) SEQUENCE CHARACTERISTICS:
        (A) LENGTH: 240 amino acids
        (B) TYPE: amino acid
        (C) STRANDEDNESS: single
        (D) TOPOLOGY: linear (xi) SEQUENCE DESCRIPTION: SEQ ID NO:11:

| Val 1 | Val | Gly | Gly | Thr 5 | Glu | Ala | Gln | Arg | Asn 10 | Ser | Trp | Pro | Ser | Gln 15 | Ile |
|---|---|---|---|---|---|---|---|---|---|---|---|---|---|---|---|
| Ser | Leu | Gln | Tyr 20 | Arg | Ser | Gly | Ser | Ser 25 | Trp | Ala | His | Thr | Cys 30 | Gly | Gly |
| Thr | Leu | Ile 35 | Arg | Gln | Asn | Trp | Val 40 | Met | Thr | Ala | Ala | His 45 | Cys | Val | Asp |
| Arg | Glu 50 | Leu | Thr | Phe | Arg | Val 55 | Val | Val | Gly | Glu | His 60 | Asn | Leu | Asn | Gln |
| Asn 65 | Asn | Gly | Thr | Glu | Gln 70 | Tyr | Val | Gly | Val | Gln 75 | Lys | Ile | Val | Val | His 80 |
| Pro | Tyr | Trp | Asn | Thr 85 | Asp | Asp | Val | Ala | Ala 90 | Gly | Tyr | Asp | Ile | Ala 95 | Leu |
| Leu | Arg | Leu | Ala | Gln 100 | Ser | Val | Thr | Leu | Asn 105 | Ser | Tyr | Val | Gln | Leu 110 | Gly |
| Val | Leu | Pro 115 | Arg | Ala | Gly | Thr | Ile 120 | Leu | Ala | Asn | Asn | Ser 125 | Pro | Cys | Tyr |
| Ile | Thr | Gly | Trp | Gly | Leu | Thr | Arg | Thr | Asn | Gly | Gln | Leu | Ala | Gln | Thr |

```
                130                     135                     140
    Leu  Gln  Gln  Ala  Tyr  Leu  Pro  Thr  Val  Asp  Tyr  Ala  Ile  Cys  Ser  Ser
    145                      150                     155                     160

Ser  Ser  Tyr  Trp  Gly  Ser  Thr  Val  Lys  Asn  Ser  Met  Val  Cys  Ala  Gly
                        165                     170                     175

Gly  Asp  Gly  Val  Arg  Ser  Gly  Cys  Gln  Gly  Asp  Ser  Gly  Gly  Pro  Leu
                   180                     185                     190

His  Cys  Leu  Val  Asn  Gly  Gln  Tyr  Ala  Val  His  Gly  Val  Thr  Ser  Phe
              195                     200                     205

Val  Ser  Arg  Leu  Gly  Cys  Asn  Val  Thr  Arg  Lys  Pro  Thr  Val  Phe  Thr
         210                     215                     220

Arg  Val  Ser  Ala  Tyr  Ile  Ser  Trp  Ile  Asn  Asn  Val  Ile  Ala  Ser  Asn
    225                     230                     235                     240
```

( 2 ) INFORMATION FOR SEQ ID NO:12:

( i ) SEQUENCE CHARACTERISTICS:
        ( A ) LENGTH: 224 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
    Ile  Ile  Gly  Gly  Val  Glu  Ser  Ile  Pro  His  Ser  Arg  Pro  Tyr  Met  Ala
    1                   5                       10                      15

His  Leu  Asp  Ile  Val  Thr  Glu  Lys  Gly  Leu  Arg  Val  Ile  Cys  Gly  Gly
                   20                      25                      30

Phe  Leu  Ile  Ser  Arg  Gln  Phe  Val  Leu  Thr  Ala  Ala  His  Cys  Lys  Gly
              35                      40                      45

Arg  Glu  Ile  Thr  Val  Ile  Leu  Gly  Ala  His  Asp  Val  Arg  Lys  Arg  Glu
         50                      55                      60

Ser  Thr  Gln  Gln  Lys  Ile  Lys  Val  Glu  Lys  Gln  Ile  Ile  His  Glu  Ser
    65                      70                      75                      80

Tyr  Asn  Ser  Val  Pro  Asn  Leu  His  Asp  Ile  Met  Leu  Leu  Lys  Leu  Glu
                        85                      90                      95

Lys  Lys  Val  Glu  Leu  Thr  Pro  Ala  Val  Asn  Val  Val  Pro  Leu  Pro  Ser
                   100                     105                     110

Pro  Ser  Asp  Phe  Ile  His  Pro  Gly  Ala  Met  Cys  Trp  Ala  Ala  Gly  Trp
              115                     120                     125

Gly  Lys  Thr  Gly  Val  Arg  Asp  Pro  Thr  Ser  Tyr  Thr  Leu  Arg  Glu  Val
         130                     135                     140

Glu  Leu  Arg  Ile  Met  Asp  Glu  Lys  Ala  Cys  Val  Asp  Tyr  Arg  Tyr  Tyr
    145                     150                     155                     160

Glu  Tyr  Lys  Phe  Gln  Val  Cys  Val  Gly  Ser  Pro  Thr  Thr  Leu  Arg  Ala
                        165                     170                     175

Ala  Phe  Met  Gly  Asp  Ser  Gly  Gly  Pro  Leu  Leu  Cys  Ala  Gly  Val  Ala
                   180                     185                     190

His  Gly  Ile  Val  Ser  Tyr  Gly  His  Pro  Asp  Ala  Lys  Pro  Pro  Ala  Ile
              195                     200                     205

Phe  Thr  Arg  Val  Ser  Thr  Tyr  Val  Pro  Trp  Ile  Asn  Ala  Val  Ile  Asn
         210                     215                     220
```

( 2 ) INFORMATION FOR SEQ ID NO:13:

( i ) SEQUENCE CHARACTERISTICS:
        ( A ) LENGTH: 223 amino acids
        ( B ) TYPE: amino acid
        ( C ) STRANDEDNESS: single ( D ) TOPOLOGY: linear ( x i ) SEQUENCE DESCRIPTION: SEQ ID NO:13:

| | | | | | | | | | | | | | | |
|---|---|---|---|---|---|---|---|---|---|---|---|---|---|---|
| Val | Val | Gly | Gly | Thr | Arg | Ala | Ala | Gln | Gly | Glu | Phe | Pro | Phe | Met | Val |
| 1 | | | | 5 | | | | | 10 | | | | | 15 | |
| Arg | Leu | Ser | Met | Gly | Cys | Gly | Gly | Ala | Leu | Tyr | Ala | Gln | Asp | Ile | Val |
| | | | 20 | | | | | 25 | | | | | 30 | | |
| Leu | Thr | Ala | Ala | His | Cys | Val | Ser | Gly | Ser | Gly | Asn | Asn | Thr | Ser | Ile |
| | | | 35 | | | | | 40 | | | | | 45 | | |
| Thr | Ala | Thr | Gly | Gly | Val | Val | Asp | Leu | Gln | Ser | Gly | Ala | Ala | Val | Lys |
| | | 50 | | | | | 55 | | | | | 60 | | | |
| Val | Arg | Ser | Thr | Lys | Val | Leu | Gln | Ala | Pro | Gly | Tyr | Asn | Gly | Thr | Gly |
| 65 | | | | | 70 | | | | | 75 | | | | | 80 |
| Lys | Asp | Trp | Ala | Leu | Ile | Lys | Leu | Ala | Gln | Pro | Ile | Asn | Gln | Pro | Thr |
| | | | | 85 | | | | | 90 | | | | | 95 | |
| Leu | Lys | Ile | Ala | Thr | Thr | Thr | Ala | Tyr | Asn | Gln | Gly | Thr | Phe | Thr | Val |
| | | | 100 | | | | | 105 | | | | | 110 | | |
| Ala | Gly | Trp | Gly | Ala | Asn | Arg | Glu | Gly | Gly | Ser | Gln | Gln | Arg | Tyr | Leu |
| | | | 115 | | | | | 120 | | | | | 125 | | |
| Leu | Lys | Ala | Asn | Val | Pro | Phe | Val | Ser | Asp | Ala | Ala | Cys | Arg | Ser | Ala |
| | | 130 | | | | | 135 | | | | | 140 | | | |
| Tyr | Gly | Asn | Glu | Leu | Val | Ala | Asn | Glu | Glu | Ile | Cys | Ala | Gly | Tyr | Pro |
| 145 | | | | | 150 | | | | | 155 | | | | | 160 |
| Asp | Thr | Gly | Gly | Val | Asp | Thr | Cys | Gln | Gly | Asp | Ser | Gly | Gly | Pro | Met |
| | | | | 165 | | | | | 170 | | | | | 175 | |
| Phe | Arg | Lys | Asp | Asn | Ala | Asp | Glu | Trp | Ile | Gln | Val | Gly | Ile | Val | Ser |
| | | | 180 | | | | | 185 | | | | | 190 | | |
| Trp | Gly | Tyr | Gly | Cys | Ala | Arg | Pro | Gly | Tyr | Pro | Gly | Val | Tyr | Thr | Glu |
| | | 195 | | | | | 200 | | | | | 205 | | | |
| Val | Ser | Thr | Phe | Ala | Ser | Ala | Ile | Ala | Ser | Ala | Ala | Arg | Thr | Leu | |
| | | 210 | | | | | 215 | | | | | 220 | | | |

( 2 ) INFORMATION FOR SEQ ID NO:14:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

| | | | | | | | | | | | | | | | |
|---|---|---|---|---|---|---|---|---|---|---|---|---|---|---|---|
| Ile | Ser | Gly | Gly | Asp | Ala | Ile | Tyr | Ser | Ser | Thr | Gly | Arg | Cys | Ser | Leu |
| 1 | | | | 5 | | | | | 10 | | | | | 15 | |
| Gly | Phe | Asn | Val | Arg | Ser | Gly | Ser | Thr | Tyr | Tyr | Phe | Leu | Thr | Ala | Gly |
| | | | 20 | | | | | 25 | | | | | 30 | | |
| His | Cys | Thr | Asp | Gly | Ala | Thr | Thr | Trp | Trp | Ala | Asn | Ser | Ala | Arg | Thr |
| | | | 35 | | | | | 40 | | | | | 45 | | |
| Thr | Val | Leu | Gly | Thr | Thr | Ser | Gly | Ser | Ser | Phe | Pro | Asn | Asn | Asp | Tyr |
| | | 50 | | | | | 55 | | | | | 60 | | | |
| Gly | Ile | Val | Arg | Tyr | Thr | Asn | Thr | Thr | Ile | Pro | Lys | Asp | Gly | Thr | Val |
| 65 | | | | | 70 | | | | | 75 | | | | | 80 |
| Gly | Gly | Gln | Asp | Ile | Thr | Ser | Ala | Ala | Asn | Ala | Thr | Val | Gly | Met | Ala |
| | | | | 85 | | | | | 90 | | | | | 95 | |
| Val | Thr | Arg | Arg | Gly | Ser | Thr | Thr | Gly | Thr | His | Ser | Gly | Ser | Val | Thr |
| | | | 100 | | | | | 105 | | | | | 110 | | |
| Ala | Leu | Asn | Ala | Thr | Val | Asn | Tyr | Gly | Gly | Gly | Asp | Val | Val | Tyr | Gly |
| | | | 115 | | | | | 120 | | | | | 125 | | |

| | | | | | | | | | | | | | | |
|---|---|---|---|---|---|---|---|---|---|---|---|---|---|---|
|Met|Ile|Arg|Thr|Asn|Val|Cys|Ala|Glu|Pro|Gly|Asp|Ser|Gly|Gly|Pro|
| |130| | | | |135| | | |140| | | | | |
|Leu|Tyr|Ser|Gly|Thr|Arg|Ala|Ile|Gly|Leu|Thr|Ser|Gly|Gly|Ser|Gly|
|145| | | | |150| | | | |155| | | | |160|
|Asn|Cys|Ser|Ser|Gly|Gly|Thr|Thr|Phe|Phe|Gln|Pro|Val|Thr|Glu|Ala|
| | | | |165| | | |170| | | | |175| | |
|Leu|Val|Ala|Tyr|Gly|Val|Ser|Val|Tyr|
| | | |180| | | | |185|

( 2 ) INFORMATION FOR SEQ ID NO:15:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

| | | | | | | | | | | | | | | |
|---|---|---|---|---|---|---|---|---|---|---|---|---|---|---|
|Ile|Ala|Gly|Gly|Glu|Ala|Ile|Thr|Thr|Gly|Gly|Ser|Arg|Cys|Ser|Leu|
|1| | | |5| | | | |10| | | | |15| |
|Gly|Phe|Asn|Val|Ser|Val|Asn|Gly|Val|Ala|His|Ala|Leu|Thr|Ala|Gly|
| | | |20| | | | |25| | | | |30| | |
|His|Cys|Thr|Asn|Ile|Ser|Ala|Ser|Trp|Ser|Ile|Gly|Thr|Arg|Thr|Gly|
| | |35| | | | |40| | | | |45| | | |
|Thr|Ser|Phe|Pro|Asn|Asn|Asp|Tyr|Gly|Ile|Ile|Arg|His|Ser|Asn|Pro|
| |50| | | | |55| | | | |60| | | | |
|Ala|Ala|Ala|Asp|Gly|Arg|Val|Tyr|Leu|Tyr|Asn|Gly|Ser|Tyr|Gln|Asp|
|65| | | | |70| | | | |75| | | | |80|
|Ile|Thr|Thr|Ala|Gly|Asn|Ala|Phe|Val|Gly|Gln|Ala|Val|Gln|Arg|Ser|
| | | | |85| | | | |90| | | | |95| |
|Gly|Ser|Thr|Thr|Gly|Leu|Arg|Ser|Gly|Ser|Val|Thr|Gly|Leu|Asn|Ala|
| | | |100| | | | |105| | | | |110| | |
|Thr|Val|Asn|Tyr|Gly|Ser|Ser|Gly|Ile|Val|Tyr|Gly|Met|Ile|Gln|Thr|
| | |115| | | | |120| | | | |125| | | |
|Asn|Val|Cys|Ala|Gln|Pro|Gly|Asp|Ser|Gly|Gly|Ser|Leu|Phe|Ala|Gly|
| |130| | | | |135| | | | |140| | | | |
|Ser|Thr|Ala|Leu|Gly|Leu|Thr|Ser|Gly|Gly|Ser|Gly|Asn|Cys|Arg|Thr|
|145| | | | |150| | | | |155| | | | |160|
|Gly|Gly|Thr|Thr|Phe|Tyr|Gln|Pro|Val|Thr|Glu|Ala|Leu|Ser|Ala|Tyr|
| | | | |165| | | | |170| | | | |175| |
|Gly|Ala|Thr|Val|Leu|
| | | |180| |

( 2 ) INFORMATION FOR SEQ ID NO:16:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

| | | | | | | | | | | | | | | |
|---|---|---|---|---|---|---|---|---|---|---|---|---|---|---|
|Ala|Asn|Ile|Val|Gly|Gly|Ile|Glu|Tyr|Ser|Ile|Asn|Asn|Ala|Ser|Leu|
|1| | | |5| | | | |10| | | | |15| |
|Cys|Ser|Val|Gly|Phe|Ser|Val|Thr|Arg|Gly|Ala|Thr|Lys|Gly|Phe|Val|
| | | |20| | | | |25| | | | |30| | |
|Thr|Ala|Gly|His|Cys|Gly|Thr|Val|Asn|Ala|Thr|Ala|Arg|Ile|Gly|Gly|
| | |35| | | | |40| | | | |45| | | |

```
Ala  Val  Val  Gly  Thr  Phe  Ala  Ala  Arg  Val  Phe  Pro  Gly  Asn  Asp  Arg
     50                       55                      60

Ala  Trp  Val  Ser  Leu  Thr  Ser  Ala  Gln  Thr  Leu  Leu  Pro  Arg  Val  Ala
65                       70                  75                           80

Asn  Gly  Ser  Ser  Phe  Val  Thr  Val  Arg  Gly  Ser  Thr  Glu  Ala  Ala  Val
               85                            90                      95

Gly  Ala  Ala  Val  Cys  Arg  Ser  Gly  Arg  Thr  Thr  Gly  Tyr  Gln  Cys  Gly
          100                           105                      110

Thr  Ile  Thr  Ala  Lys  His  Val  Thr  Ala  Asn  Tyr  Ala  Glu  Gly  Ala  Val
          115                      120                           125

Arg  Gly  Leu  Thr  Gln  Gly  Asn  Ala  Cys  Met  Gly  Arg  Gly  Asp  Ser  Gly
     130                      135                      140

Gly  Ser  Trp  Ile  Thr  Ser  Ala  Gly  Gln  Ala  Gln  Gly  Val  Met  Ser  Gly
145                      150                 155                           160

Gly  Asn  Val  Gln  Ser  Asn  Gly  Asn  Asn  Cys  Gly  Ile  Pro  Ala  Ser  Gln
               165                      170                      175

Arg  Ser  Ser  Leu  Phe  Glu  Arg  Leu  Gln  Pro  Ile  Leu  Ser  Gln  Tyr  Gly
               180                 185                           190

Leu  Ser  Leu  Val  Thr  Gly
               195
```

(2) INFORMATION FOR SEQ ID NO:17:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:17:

```
Gly  Asn  Ser  Gly  Gly  Ala  Leu
1                 5
```

(2) INFORMATION FOR SEQ ID NO:18:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:18:

```
Gly  Asp  Ser  Gly  Gly  Pro  Lys
1                 5
```

(2) INFORMATION FOR SEQ ID NO:19:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:19:

```
Met  Lys  Lys  Thr  Arg  Phe  Val  Leu  Asn  Ser  Ile  Ala  Leu  Gly
1                 5                           10
```

(2) INFORMATION FOR SEQ ID NO:20:

(i) SEQUENCE CHARACTERISTICS:
    (A) LENGTH: 22 base pairs
    (B) TYPE: nucleic acid
    (C) STRANDEDNESS: single
    (D) TOPOLOGY: linear -continued (x i) SEQUENCE DESCRIPTION: SEQ ID NO:20:

CGCTCCACCA GCATTACCGC GG                                                    2 2

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:21:

ATCAATAACA GCATTATTGG T                                                     2 1

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:22:

TAATGCAATT GCTGATAGTT C                                                     2 1

(2) INFORMATION FOR SEQ ID NO:23:

(i) SEQUENCE CHARACTERISTICS:
        (A) LENGTH: 11 amino acids
        (B) TYPE: amino acid
        (C) STRANDEDNESS: single
        (D) TOPOLOGY: linear (x i) SEQUENCE DESCRIPTION: SEQ ID NO:23:

Lys Phe Phe Phe Gly Asp Arg Phe Ala Glu Gln
1               5                       10

ANALOG OF HAEMOPHILUS HIN47 WITH REDUCED PROTEASE ACTIVITY

REFERENCE TO RELATED APPLICATION

This application is a continuation-in-part of U.S. patent application Ser. No. 08/296,149 filed Aug. 26, 1994, which itself is a continuation-in-part of Ser. No. 08/278,091 filed Jul. 21, 1994 (now U.S. Pat. No. 5,506,139).

FIELD OF THE INVENTION

The present invention relates to the field of immunology and is particularly concerned with immunogens and antigens from species of Haemophilus.

BACKGROUND TO THE INVENTION

*Haemophilus influenzae* is the organism responsible for a variety of serious human diseases, such as meningitis, epiglotitis, pneumonia and otitis media. *Haemophilus influenzae* type b (Hib) is a major cause of bacterial meningitis in children under the age of five years. Protective antibodies to the disease are induced by the capsular polysaccharide of the organism and vaccines have been developed that utilise the purified polyribosyl ribitol phosphate (PRP) as the antigen. This vaccine provides 90% protection in adults and in children over 24 months of age, but was ineffective in children under 24 months (Zangwill et al 1993). (The references are identified in a list of references at the end of this disclosure, each of which reference in the list is hereby incorporated by reference without further reference thereto). Like other polysaccharide antigens, PRP does not induce the proliferation of T-helper cells, and re-immunisation fails to elicit either a booster response or an increase in memory cells. Conjugation of the PRP polysaccharide with protein carriers confers T-cell dependent characteristics to the vaccine and substantially enhances the immunologic response to the PRP antigen. Currently, there are four PRP-carrier conjugate vaccines available. These are vaccines based upon *H. influenzae* type b capsular polysaccharide conjugated to diphtheria toxoid, tetanus toxoide, or *Nelsseria meningitidis* outer membrane protein (reviewed in Zangwill et al, 1993). These *H. influenzae* b conjugate vaccines have dramatically reduced the incidence of bacterial meningitis (Schoendorf et al, 1994).

There are six serotypes of *H. influenzae* designated a to f, which are defined by their capsular polysaccharides. The current Haemophilus conjugate vaccines do not protect against other invasive typable strains (types a and c) and, importantly, do not protect against non-typable (NTHi) strains which are a common cause of postpartum and neonatal spsis, pneumonia and otitis media. Otitis media is the most common illness of early childhood with approximately 70% of all children suffering at least one bout of otitis media before the age of seven. Chronic otitis media can lead to hearing, speech, and cognitive impairment in children. It is caused by bacterial infection with *Streptococcus pneumonia* (approximately 50%), non-typable *H. influenzae* (approximately 30%), and *Moraxella* (*Branhamella*) *catarrhalis* (approximately 20%). In the United States alone, treatment of otitis media costs between 1 and 2 billion dollars per year for antibiotics and surgical procedures, such as tonsillectomies, adenoidectomies and insertion of tympanostomy tubes. To achieve universal protection against *H. influenzae* related diseases, particularly in the two to six month age group and certain high risk groups, the provision of conserved, cross-reactive non-capsular *H. influenzae* immunogens is desirable. Non-typable strains of *H. influenzae* are also important pathogens responsible for pneumonia in the elderly and other individuals who are particularly susceptible to respiratory infections. There is thus a need for antigens from *H. influenzae* which are useful as components in immunogenic preparations that provide protection against the many serotypes of *H. influenzae*. PCT application WO 92/10936, published Jul. 9, 1992 and incorporated herein by reference thereto, describes a 47,000 molecular weight outer membrane protein obtained from *H. influenzae* that is reported to be an adhesin and has been termed Hin47 that is immunologically conserved between non-typable, type b and non-typed clinical isolates of *H. influenzae*. The amino acid sequence of Hin47 and the nucleotide sequence of the gene encoding Hin47 were presented at the American Society of Microbiology (ASM) conference held in New Orleans, May 26–30, 1992. These sequences have also been published in PCT application WO 94/00149, published Jan. 6, 1994 and incorporated herein by reference thereto.

Since Hin47 is conserved among strains of *Haemophilus influenzae*, and is reported to be an adhesin, the protein has utility in diagnosis of and vaccination against disease caused by *H. influenzae* or other bacterial pathogens that produce Hin47 or a protein capable of raising antibodies specifically reactive with Hin47.

A disadvantage of Hin47 for use as an antigen in diagnosis, for the generation of anti-Hin47 antibodies useful in diagnosis and as an immunogen in vaccination is the unexpected discovery by the present applicants that Hin47 has protease activity which results in the autodigestion of Hin47 and the proteclytic degradation of other antigens mixed therewith.

It would be advantageous to provide analogs of Hin47 protein (sometimes referred to herein as mutants or derivatives) that are substantially reduced in proteolytic activity for use as antigens, immunogenic preparations including vaccines, carriers for other immunogens and the generation of diagnostic reagents.

SUMMARY OF THE INVENTION

The present invention is directed towards the provision of analogs of Haemophilus Hin47 protein having reduced protease activity.

In accordance with one aspect of the invention there is provided an isolated and purified analog of *Haemophilus influenzae* Hin47 protein having a decreased protease activity which is less than about 10% of natural Hin47 protein. Such Hin47 analog preferably has substantially the same immunogenic properties of natural Hin47 protein. The analog of the present invention may be produced by chemical, biochemical or genetic modification of natural Hin47.

In one embodiment of the present invention, when the analog is produced by genetic modification, at least one amino acid of the natural Hin47 contributing to protease activity may be deleted or replaced by a different amino acid to produce the reduced protease activity. Alternatively, the reduced protease activity may be achieved by inserting at least one amino acid into the natural Hin47 protein. The at least one deleted or replaced amino acid may be selected from amino acids 195 to 201 of Hin47, and specifically may be Serine-197, which may be deleted or replaced by alanine cysteine or threonine. In addition, the at least one deleted or replaced amino acid may be His-91 and may be deleted or replaced by alanine or lysine or arginine. Further, the at least one deleted or replaced amino acid may be Asp-121 and may be deleted or replaced by alanine.

In addition, multiple amino acids in the Hin47 molecule may be deleted or replaced. Such multiple amino acids may include His-91 and Serine-197 and may be deleted or replaced by Ala-91 and Ala-197 to produce a Hin47 analogue H91A/S197A. In addition, the multiple amino acids may include His-91, Asp-121 and Ser-197 and may be deleted or replaced with Ala-91, Ala-121 and Ala-197 respectively to produce a Hin47 analogue H91A/D121A/S197A. A summary of some of the properties of some Hin47 analogues as provided herein is shown in Table 3. Only one Hin47 mutant D121E was found to retain substantial protease activity.

In a further aspect, the present invention provides an isolated and purified nucleic acid molecule comprising a mutant *Haemophilus influenzae* hin47 gene encoding an analog of *Haemophilus influenzae* Hin47 protein having a reduced protease activity which is less than about 10% of natural Hin47 protein. The mutant hin47 gene may encode any of the Hin47 analogs discussed above. The mutant gene preferably is formed by site-directed mutagenesis of a wild-type hin47 gene. The nucleic acid molecule may be contained in a recombinant plasmid adapted for transformation of a host and may be plasmid DS-1011-1-1 (deposited on Jul. 27, 1994 at American type Culture Collection under Accession No. 75845. The invention also includes a transformed cell containing such a recombinant plasmid.

The present invention, in another aspect, includes a method for producing an analog of *Haemophilus influenzae* Hin47 protein having a reduced protease activity which is less than about 10% of natural Hin47 protein, which comprises identifying at least one amino acid residue of Hin47 protein which contributes to protease activity thereof, effecting site-directed mutagenesis of the hin47 gene to remove or replace a nucleotide sequence encoding the at least one amino acid and to produce a mutated hin47 gene, introducing the mutated hin47 gene into a cell to produce a transformed cell and growing the transformed cell to produce the Hin47 analog. The at least one amino acid which is selected may be any of the ones specifically identified above with respect to the Hin47 analog.

The introduction of the mutated hin47 gene preferably produces a transformed cell in which the mutated hin47 gene is under control of the T7 promoter and the growing of the transformed cell and expression of the Hin47 analog by the T7 promoter then preferably is effected by culturing in an inducing concentration of lactose. Preferably, the introduction of the mutated hin47 is effected by transforming the cell with the recombinant plasmid DS-1011-1-1, sometimes otherwise referred to as plasmid pT7/Hin47*.

A further aspect of the invention provides a method of providing isolated and purified Hin47 analog, which comprises effecting the procedure described above for the production of the Hin47 analog to produce grown transformed cells harbouring inclusion bodies containing the Hin47 analog, disrupting the grown transformed cells to produce supernatant and the inclusion bodies, solubilizing the inclusion bodies to produce a solution containing Hin47 analog, chromatographically purifying the Hin47 analog from the solution free from cell debris, and isolating the purified Hin47 analog.

The analogs of Hin47 provided herein with their decreased proteolytic activity are useful as antigens in immunogenic composition, carriers for other immunogens, diagnostic agents and in the generation of diagnostic agents. The nucleic acid molecules also are useful as probes for diagnostic use and also as in immunogenic compositions.

In a further aspect of the invention, there is provided an immunogenic composition comprising an immuno-effective amount of the Hin47 analog or of the nucleic acid molecule including the gene encoding the Hin47 analog. The immunogenic composition may be formulated as a vaccine for in vivo administration to a host, including a human, to confer protection against diseases caused by a bacterial pathogen that produces Hin47 or a protein capable of inducing antibodies in the host specifically reactive with Hin47. The bacterial pathogen may be a Haemophilus species, such as *Haemophilus influenzae*. The immunogenic compositions of the invention may further comprise at least one other immunogenic or immunostimulating material, such as an adjuvant. In an additional embodiment, the nucleic acid molecule comprising a gene encoding the Hin47 analog may be contained within a live vector, such as a pox virus, Salmonella, poliovirus, adenovirus, vaccinia or BCG.

The invention also extends to a method of generating an immune response in a host, including a human, comprising administering thereto an immuno-effective amount of the immunogenic compositions provided herein.

As mentioned above, the Hin47 analog provided herein is useful in diagnostic applications. Accordingly, in an additional aspect of the invention, there is provided a method of determining the presence of antibodies specifically reactive with Hin47 in a sample, comprising the steps of:

(a) contacting the sample with the Hin47 analog having substantially the same immunogenic properties as the natural Hin47 protein as provided herein to produce complexes comprising the Hin47 analog and any such antibodies present in the sample specifically reactive therewith; and (b) determining production of the complexes.

The present invention also provides a method of determining the presence of Hin47 in a sample, comprising the steps of:

(a) immunizing a subject with an immunogenic composition as provided herein to produce antibodies specific for Hin47 protein;

(b) contacting the sample with the antibodies to produce complexes comprising any Hin47 present in the sample and the Hin47 specific antibodies; and (c) determining production of the complexes.

The invention also extends to a diagnostic kit for determining the presence of antibodies in a sample specifically reactive with Hin47, comprising:

(a) the Hin47 analog having substantially the same immunogenic properties as the natural Hin47 protein as provided herein;

(b) means for contacting the analog with the sample to produce a complex comprising the analog and any such antibodies present in the sample; and (c) means for determining production of the complex.

BRIEF DESCRIPTION OF THE DRAWINGS

FIGS. 2A, 2B, 2C, 2D, 2E, 2F, 2G and 2H show the full nucleotide (SEQ ID NO: 1) and deduced amino acid sequence (SEQ ID NO: 2) of Hin47 from *H. influenzae* strain SB33 as well as a partial nucleotide sequence (SEQ ID NO: 3) and a partial deduced amino acid sequence (SEQ ID NO: 4) thereof, the latter being specifically copied by an inventor herein from materials presented in the ASM conference as described above;

FIGS. 3A and 3B show a comparison of the amino acid sequences of *H. influenzae* Hin47 (SEQ ID NO: 2), *E. coli* htrA (SEQ ID NO: 5), and *Salmonella typhimurium* htrA (SEQ ID NO: 6);

FIGS. 4A, 4B, 4C, 4D and 4E show an alignment of amino acid residues 57 to 256 of Hin 47 with certain known proteases (SEQ ID NOS: 7 to 16). Codes are as follows: TON, rat tonin; PKAAB, kallikrein; PTN, trypsin; CHAA, chymotrypsin; EST, elastase: RP2A, rat mast cell protease; SGT, *Streptomyces griseus* trypsin; SGBE, *S. griseus* proteinase A; SGA, *S. griseus* proteinase B; ALP, *L. enzymogenes* alpha-lytic protease; hin47, res. 57–256 of Hin47. Asterisks(*) denote structurally conserved regions. The catalytic triad residues are indicated by a hash mark (#). 'con' refers to regions of structural concensus, among the mammalian proteases;

FIG. 7, comprising panels A, B and C, shows the protease activities of natural Hin47 and Hin47 analog towards β-casein;

FIG. 8, comprising panels A, B and C shows the stability of natural Hin47 and the Hin47 analog at different temperatures;

FIG. 9, comprising panels A, B, and C, and D shows the enzymatic degradation of an *H. influenzae* recombinant protein by natural Hin47 and the Hin47 analog.

FIG. 11 shows the amino acid comparison of Hin47 protein isolated from *H. influenzae* strains SB33 and SB12.

GENERAL DESCRIPTION OF INVENTION

Any Haemophilus strains that have Hin47 genes may be conveniently used to provide the purified and isolated nucleic acid molecules (which may be in the form of DNA molecules), comprising at least a portion coding for Hin47 as typified by embodiments of the present invention. Such strains are generally available from clinical sources and from bacterial culture collections, such as the American Type Culture collection. Such strains include *H. influenzae* strains and other bacteria that produce a protein capable of generating antibodies that specifically recognize Hin47 fragment or analog thereof. Appropriate strains of Haemophilus may include:

*H. influenzae* type b strain MinnA;

*H. influenzae* type b strain Eagan;

*H. influenzae* non-typable strain SB33;

*H. influenzae* non-typable strain SB12; or

*H. influenzae* non-typable strain PAK 12085.

Figure 1:
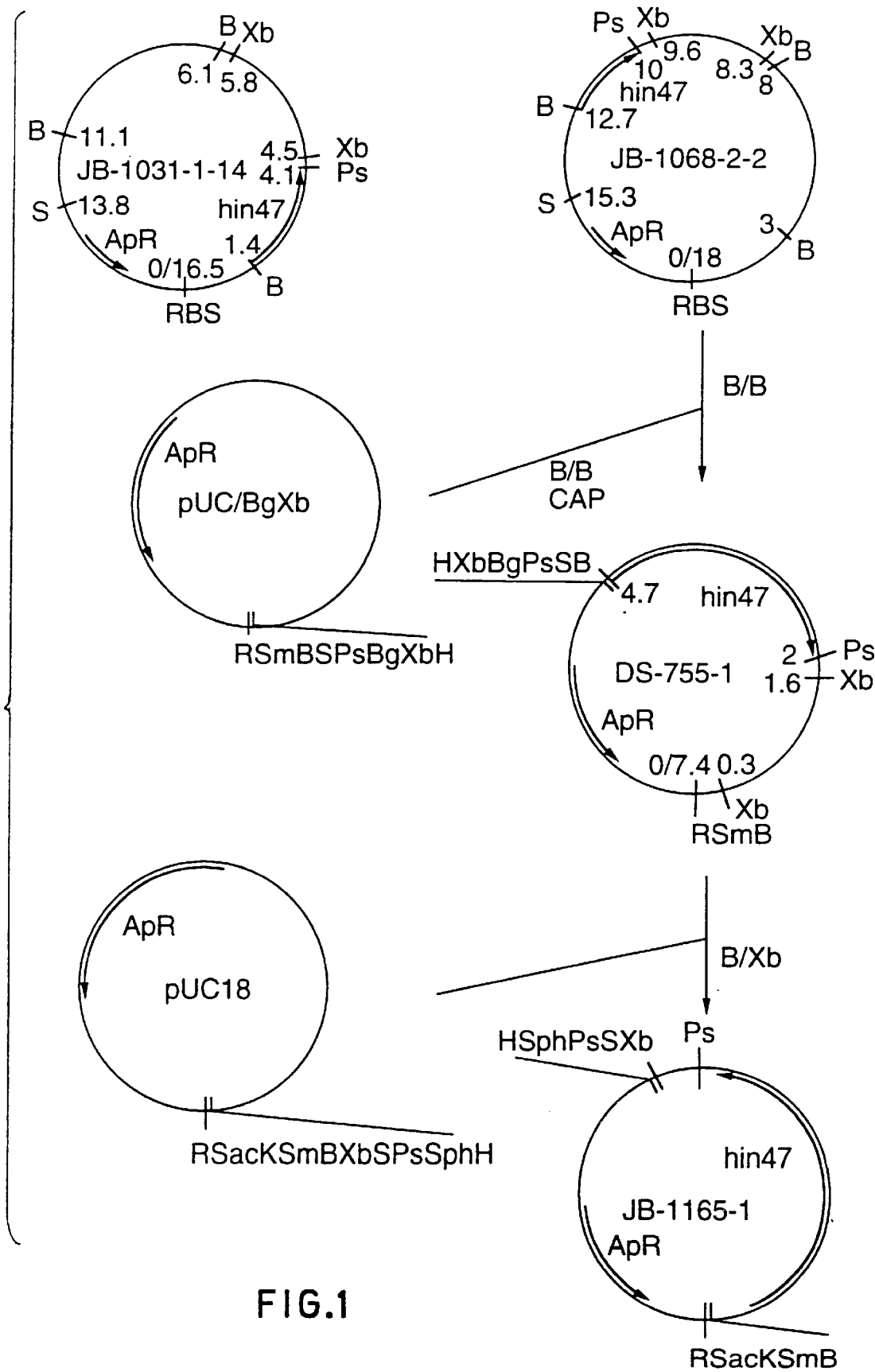
FIG. 1 shows the restriction maps of plasmids JB-1031-1-14 and JB-1068-2-2 and the construction of the plasmids for sequence analysis.

Referring to FIG. 1, there is illustrated restriction maps of plasmids JB-1031-1-14 and JB-1068-2-2 that contain a portion encoding Hin47 protein from non-typable *H. influenzae* SB33. The nucleotide sequence of the Hin47 gene was determined and is shown in FIG. 2 along with the deduced amino acid sequence of the Hin47 protein. Referring to FIG. 3, there is shown an amino acid sequence alignment of *H. influenzae* Hin47 and the serine proteases htrA from *Escherichia coli* and htrA from *Salmonella typhimurium*. This alignment for the first time reveals the unexpected discovery of the present applicants that Hin47 is related to bacterial serine proteases and that Hin47 has protease activity. Hin47 has previously been reported to be an adhesin. The discovered protease activity thereof greatly limits the usefulness of natural Hin47 as an immunogen for vaccination and as an antigen in diagnostic uses. The sequence alignment shown in FIG. 3 revealed that the htrA proteins and Hin47 contain a GNSGGAL (SEQ ID NO: 17) sequence between residues 195 and 201 of the mature protein. The consensus sequence of the active site of serine proteases is GDSGGPK (SEQ ID NO: 18) (Brenner, 1988) and the active residue is serine. Thus, Serine-197 in Hin47 was mutated to produce an analog of Hin47 reduced in protease activity, in accordance with one embodiment of the invention. In a particular embodiment, Serine-197 was replaced by alanine. Amino acid residues 57 to 256 of Hin47 were further aligned with known proteases and the active site residues identified from the local homologies surrounding the residues of the catalytic traid (FIG. 4). There is a standard numbering system for serine proteases in which the catalytic triad residues are numbered as His-57, Asp-102 and Ser-195. These correspond to residues His-91, Asp-121 and Ser-197 in the sequential numbering system. Thus, referring to FIG. 4, there is shown a structure-based alignment of ten structurally determined serine proteases (SEQ ID NOS: 7 to 16) in which homologous residues are aligned primarily on the basis of similar locations in three-dimensional space. The location of many of the residues in the hydrophobic core of Hin47, as well as residues around the active site can be aligned reasonably well to identify functional amino acids of the Hin47 protease. Thus, other amino acid residues in Hin47 that contribute to protease activity of the protein include His-91 and Asp-121. In particular embodiments, His-91 may be replaced by alanine, lysine or arginine. In an additional embodiment, Asp-121 may be replaced by alanine or glutamic acid. In an additional embodiment, Serine-197 may be replaced by alanine, serine or threonine. Although the provision of an analog of Hin47 having reduced protease activity has been exemplified herein by particular amino acid substitution within Hin47 protein, the discovery of the protease activity and the methods of Hin47 expression, purification and analysis provided herein, allow for the production of other analogs having at least one other amino acid deleted or replaced or having at least one additional amino acid inserted into the Hin47 protein. In particular applications and embodiments, it may be desirable to simultaneously alter several amino acids of the Hin47 protein to particularly reduce the protease activity of Hin47. The multiple amino acids may be His-91 and Ser-197 and may be deleted or replaced by alanine. In an alternative embodiment, the multiple amino acids may be His-91, Asp-121 and Ser-197 and may be deleted or replaced by alanine. Accordingly, the present invention provides analogs of Hin47 protein having decreased protease activity due to single or multiple amino acid deletions, replacements or additions within the Hin47 protein.

As discussed above, Hin47 shows homology with *E. coli* htrA or *S. typhimurium* htrA, both of which are stress response proteins with serine protease activity. *E. coli* htrA is inducible by growth at 43.5° C. (ref. 13). We have shown that the *E. coli* htrA protein is also inducible by growth in 6% ethanol. Hin47 can also be induced by 6% ethanol and to a lesser extent by temperature reduction at 43.5° C. as described in detail below. This analysis of the expression of Hin47 provides further evidence of the relatedness between this protein and LtrA.

The hin47 gene was also cloned from the non-typable *H. influenzae* strain SB12 by PCR amplification. Referring to FIG. 11, there is shown an amino acid compariosn between the Hin47 proteins of *H. influenzae* strains SB12 and SB33. This shows the proteins to be almost identical in amino acid sequence.

Figure 5A:
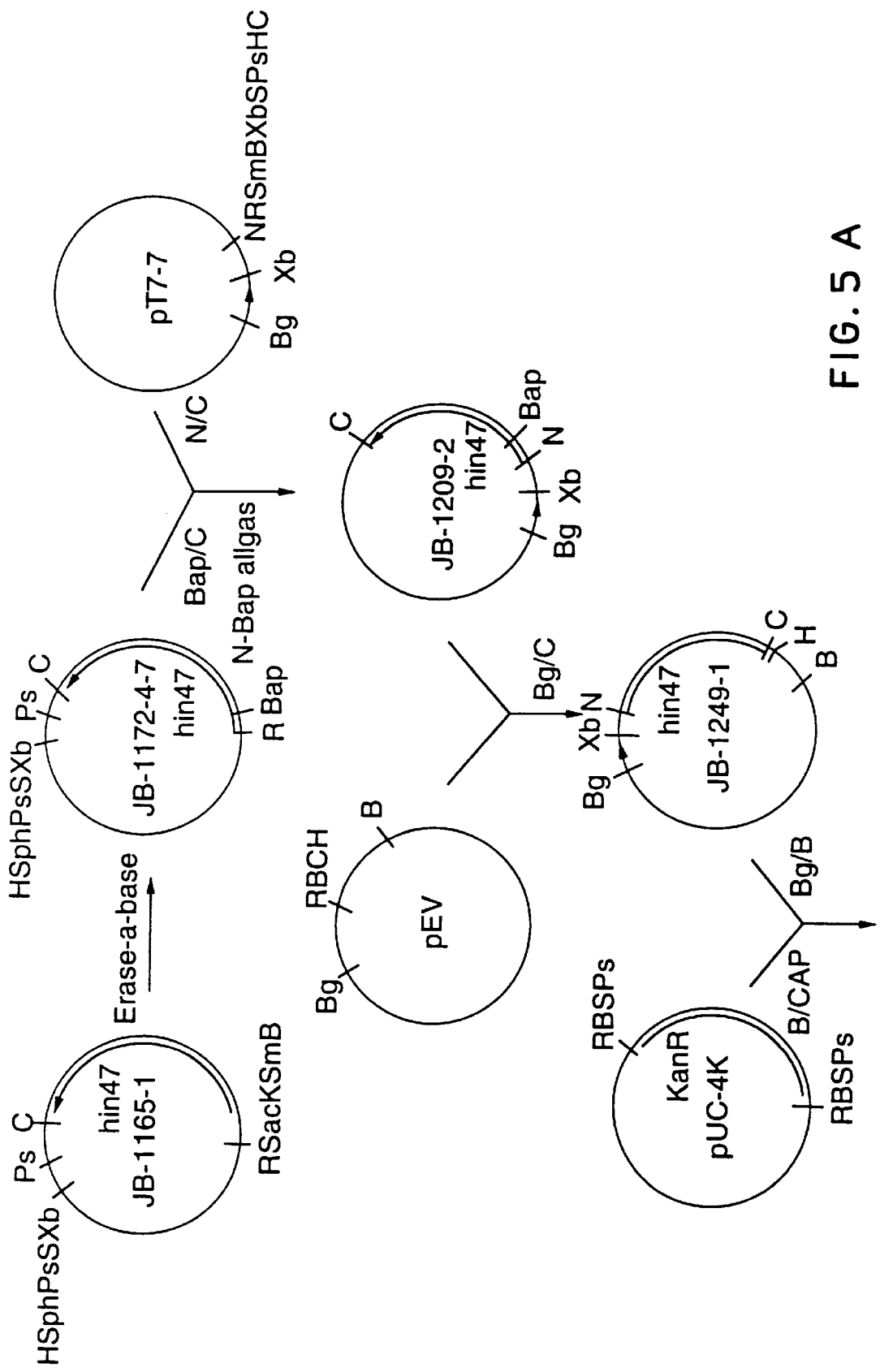
FIGS. 5A and 5B show the restriction maps for plasmids DS-1011-1-1 and DS-1048-2 which express a Hin47 analog from *E. coli* and a construction scheme for plasmid DS-1011-1-1 (plasmid pT7/Hin47*)
Figure 5B:
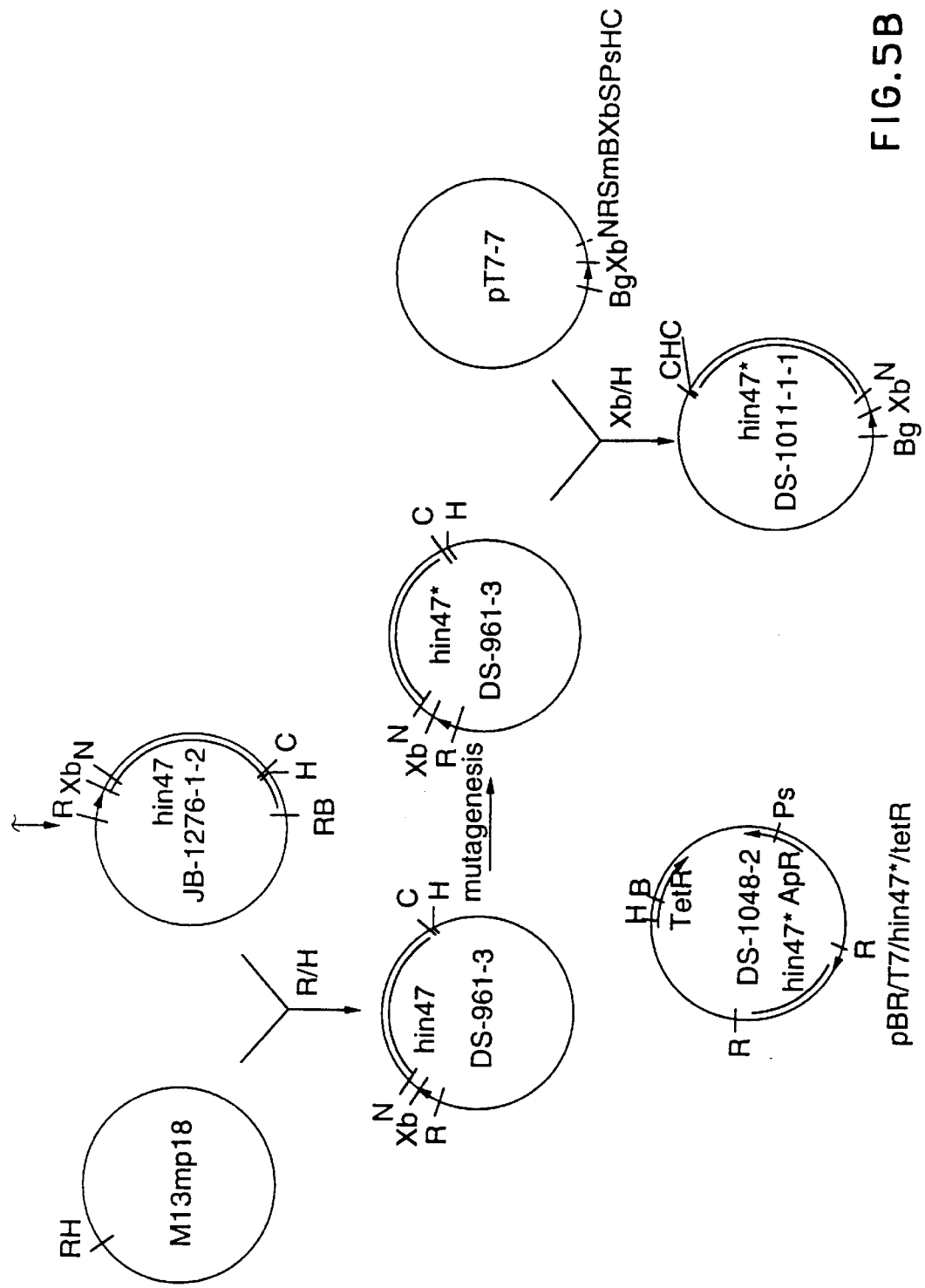
Figures 6A, 6B:
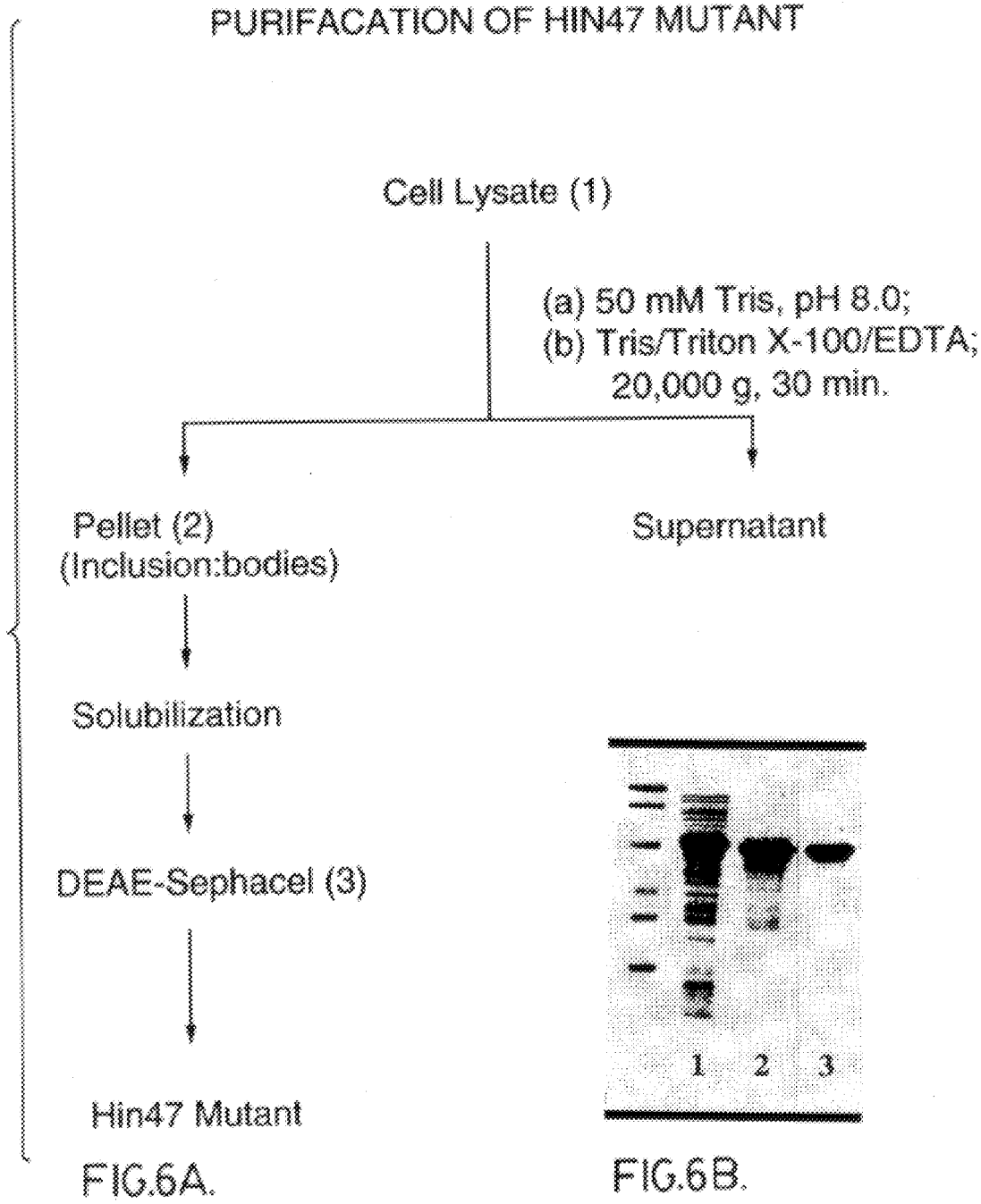
FIG. 6, comprising panels A and B shows a process for purifying the Hin47 analog from *E. coli* according to one embodiment of the present invention (panel A) and gel analysis (panel B) of the purified product.

Referring to FIG. 5, there is illustrated plasmids DS-1011-1-1 and DS-1048-2 which express a Hin47 analog serine-197→alanine in *E. coli*. FIG. 6 shows a flow diagram of a method for the purification of the Hin47 analog from *E. coli* inclusion bodies.

FIG. 7 shows the reduced protease activity of the Hin47 serine-197→alanine analog on the substrate β-casein and demonstrates the analog to have less than about 10% of the protease activity of natural Hin47 protein. Thus, in one embodiment of the invention, there is provided an analog of Hin47 having a protease activity of less than about 10% of the protease activity of natural Hin47 and such analog may specifically have amino acid Serine-197 replaced by alanine.

Referring to FIG. 8, there is illustrated an analysis of the increased stability of an analog of Hin47 as provided herein. Thus, in one embodiment of the present invention, there is provided an analog of Hin47 protein having increased thermal stability, and such analog may specifically have amino acid serine-197 replaced by alanine.

Referring to FIG. 9, there is illustrated the proteolytic degradation of a non-Hin47 Haemophilus antigen by Hin47 and a Hin47 analog as provided herein. Thus, in accordance with a further embodiment of the present invention, there is provided an analog of Hin47 compatible with a second non-Hin47 protein and such analog may specifically have amino acid Serine-197 replaced by alanine.

Figure 10A:
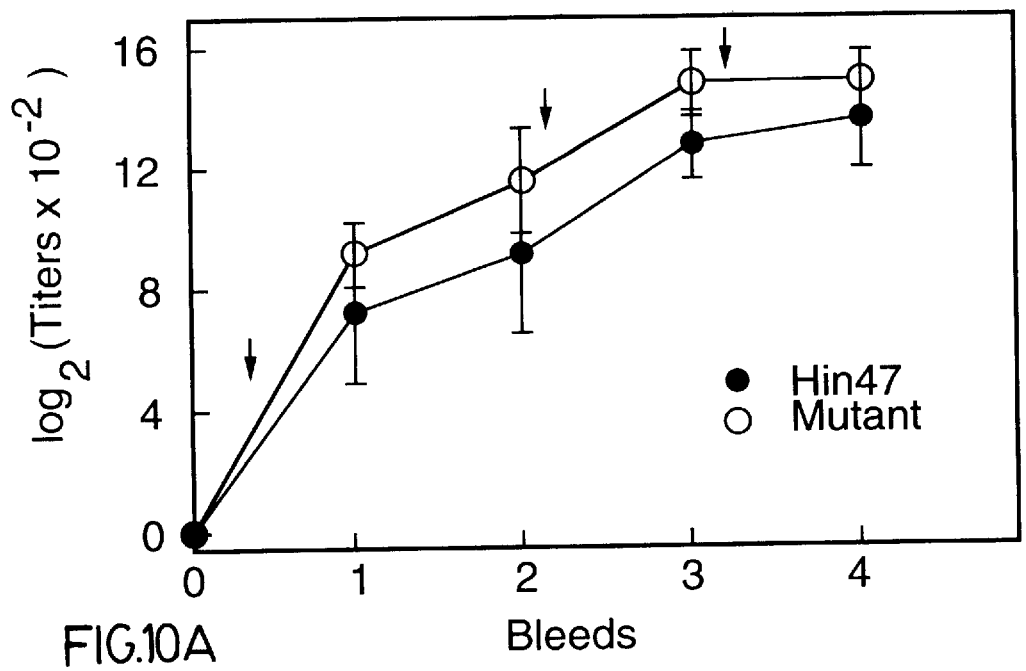
FIG. 10, comprising panels A, and B shows the comparative immunogenicity of natural Hin47 and the Hin47 analog in mice.
Figure 10B:
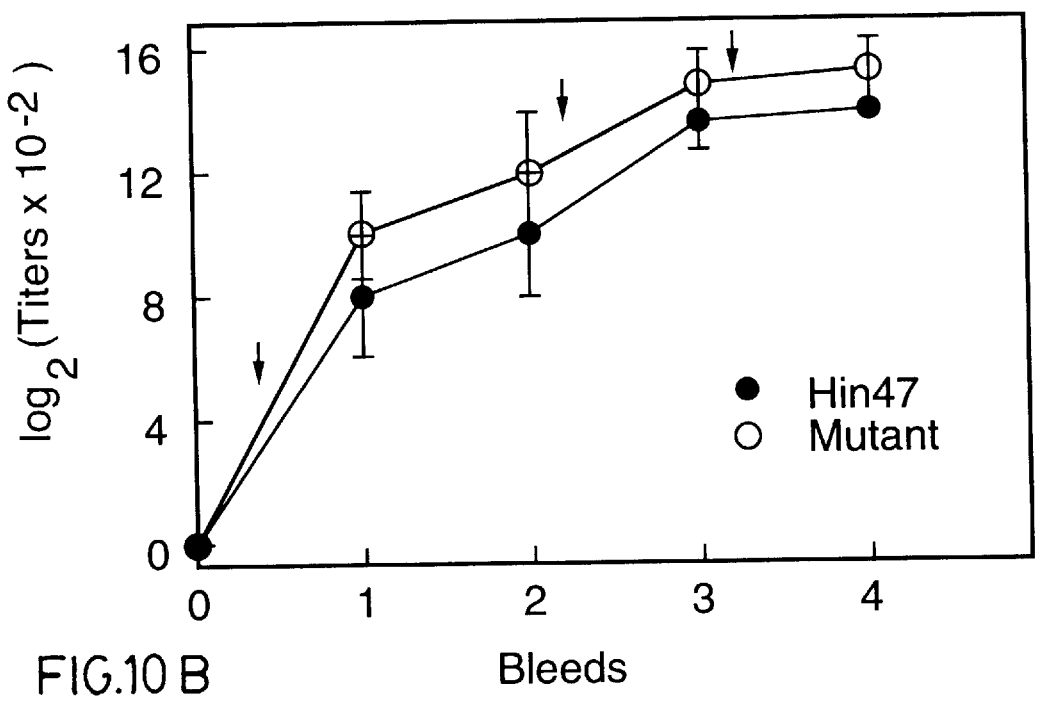
Figure 12:
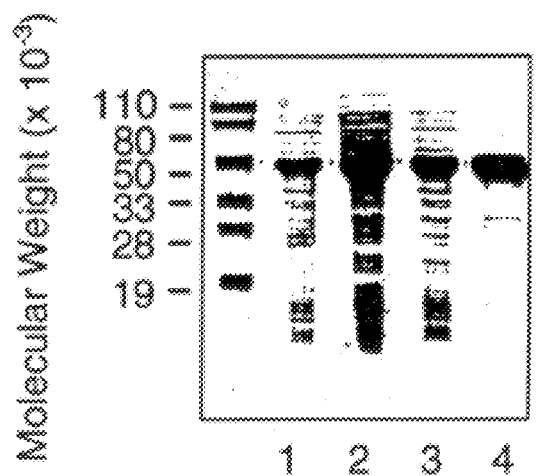
FIG. 12 shows the purification of the Hin47 analogue H91A from *E. coli*.

Referring to FIG. 10 and Table 1, there is illustrated the comparative immunogenicity of unmodified Hin47 and a Hin47 analog having reduced protease activity in mice. The Hin47 protein and Hin47 analogs S197A and H91A had comparable immunogenicity. Thus, in a particular embodiment, there is provided an analog of Hin47 having reduced protease activity and having substantially the same immunogenic properties of natural Hin47 protein. Such analog may specifically have amino acid Serine-197 replaced by alanine.

Referring to Tables 2 and 3, there is shown the immunoprotective properties of analogs of Hin47 having reduced protease activity against Hib in the infant rat model of bacteraemia and in the active immunization chinchilla model of otitis media according to particular embodiments of the invention, such analog may specifically have amino acid His-91 deleted or replaced by alanine, lysine or arsinine; Asp-121 deleted or replaced by alanine or glutamic acid; Serine-197 replaced by alanine, cysteine or threonine; or combination thereof.

In accordance with another aspect of the present invention, there is provided a vaccine against Haemophilus or other bacterial pathogens that produce Hin47 or a protein capable of inducing antibodies that specifically recognize Hin47, comprising an immunogenically-effective amount of an immunoprotective analog of Hin47 as provided herein or a nucleic acid molecule having a sequence encoding a Hin47 analog as provided herein, and a physiologically-acceptable carrier therefor. The provided analogs also may be used as a carrier protein for hapten, polysaccharides or peptides to make a conjugate vaccine against antigenic determinants unrelated to Hin47.

As will be apparent from the following disclosure, the present invention further provides plasmids and novel strains of bacteria for production of Hin47 analogs as provided herein.

The purified and isolated DNA molecules comprising at least a portion coding for an analog of *Haemophilus influenzae* Hin47 protein having reduced protease activity compared to natural Hin47 typified by the embodiments described herein, are advantageous as nucleic acid probes for the specific identification of Haemophilus strains in vitro or in vivo. The Hin47 analogs encoded by the DNA molecules provided herein are useful as diagnostic reagents as antigens or for the generation of anti-Hin47 antibodies, antigens for the vaccination against the disease caused by species of Haemophilus and other bacterial pathogens that produce a protein capable of producing antibodies that specifically recognise Hin47 and for detecting infection by Haemophilus and other such bacteria.

In additional embodiments of the present invention, the Hin47 analogs having reduced protease activity as provided herein may be used as carrier molecules to prepare chimeric molecules and conjugate vaccines (including glycoconjugates) against pathogenic bacteria, including encapsulated bacteria. Thus, for example, glycoconjugates of the present inventions may be applied to vaccinations to confer protection against disease and infection caused by any bacteria having polysaccharide antigens including lipooligosaccharides (LOS) and PRP. Bacterial pathogens may include, for example, *Haemophilus influenzae, Streptococcus pneumoniae, Escherichia coli, Nelsseria maningitidis, Salmonella typhi, Streptococcus mutans, Cryptococcus neoformans*, Klebsiella, *Staphylococcus aureus* and *Pseudomonas aeruglnosa*. Particular antigens which can be conjugated to analogs of Hin47 and methods to achieve such conjugations are described in applicants published PCT application WO 94/12641 which is hereby incorporated by reference thereto.

In another embodiment, the carrier function of Hin47 analogs may be used, for example, to induce immunity toward abnormal polysaccharides of tumor cells, or to produce anti-tumor antibodies that can be conjugated to chemotherappeutic or bioactive agents.

Accordingly, the present invention provides the primary sequence and the preparation of analogs of Hin47 of *H. influenzae* that can be used in the prevention and diagnosis of diseases caused by *H. influenzae*. In particular, the inventors discovered that the Hin47 analogs can elicit protective immune responses against live *H. influenzae* type b bacterial challenge. Thus, the present inventions have utility in vaccines. The invention also discloses the nucleotide sequences of the genes encoding the Hin47 analogs. These DNA segments may be used to provide an immunogen essentially free from other *H. influenzae* antigens, such as PRP and lipooligosaccharides (LOS), through the application of recombinant DNA technology. The Hin47 analog protein, may be produced in a suitable expression system, such as *E. coli*, Haemophilus, Bacillus, Bordetella Fungi, Yeast, Baculovirus, Poxvirus, vaccinia or mammalian expression systems. The present disclosure further provides novel techniques which can be employed for preparing essentially pure Hin47 analogs.

It is clearly apparent to one skilled in the art, that the various embodiments of the present invention have many applications in the fields of vaccination, diagnosis, treatment of, for example, Haemophilus infections, and infections with other bacterial pathogens that produce proteins capable of producing antibodies that specifically recognize Hin47 and the generation of immunological reagents. A further non-limiting discussion of such uses is further presented below.

1. Vaccine Preparation and Use

Immunogenic compositions, suitable to be used as vaccines, may be prepared from Hin47 analogs as disclosed herein. The vaccine elicits an immune response in a subject which produces antibodies, including anti-Hin47 antibodies and antibodies that are opsonizing or bactericidal. Should the vaccinated subject be challenged by Haemophilus or other bacteria that produce proteins capable of producing antibodies that specifically recognize Hin47, the antibodies bind to and inactivate the bacterium. Furthermore, opsonizing or bactericidal anti-Hin47 antibodies may also provide protection by alternative mechanisms.

Immunogenic compositions including vaccines may be prepared as injectables, as liquid solutions or emulsions. The Hin47 analogs may be mixed with pharmaceutically acceptable excipients which are compatible with the Hin47 analog. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Methods of achieving adjuvant effect include the use of agents such as aluminum hydroxide or phosphate (alum), commonly used as 0.05 to 0.1 percent solution in phosphate buffered saline. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the Hin47 analogs. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the Hin47 analogs. Suitable regimes for initial administration and booster doses are also variable, but may include an initial administration followed by subsequent administrations. The dosage may also depend on the route of administration and will vary according to the size of the host.

The concentration of antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

The nucleic acid molecules encoding the Hin47 analog of the present invention may also be used directly for immunization by administration of the DNA directly, for example, by injection for genetic immunization or by constructing a live vector, such as Salmonella, BCG, adenovirus, poxvirus, vaccinia or poliovirus. A discussion of some live vectors that have been used to carry heterologous antigens to the immune system are discussed in, for example, O'Hagan (1992). Processes for the direct injection of DNA into test subjects for genetic immunization are described in, for example, Ulmer et al, 1993.

2. Immunoassays

The Hin47 analogs of the present invention are useful as immunogens for the generation of anti-Hin47 antibodies, as antigens in immunoassays including enzyme-linked immunosorbent assays (ELISA), RIAs and other non-enzyme linked antibody binding assays or procedures known in the art for the detection of anti-bacterial, Haemophilus, and anti-Hin47 antibodies. In ELISA assays, the Hin47 analogs, are immobilized onto a selected surface, for example, a surface capable of binding proteins such as the wells of a polystyrene microtiter plate. After washing to remove incompletely adsorbed Hin47 analogs, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound Hin47 analogs, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

3. Use of Sequences as Hybridization Probes

The nucleic acid molecules of the present invention, having the sequence of the hin47 analog gene, allow for the identification and cloning of the Hin47 genes from any species of Haemophilus and other bacteria that produce proteins capable of producing antibodies that specifically recognize Hin47.

The nucleic acid molecules having the sequence encoding the Hin47 analog of the present invention are useful for their ability to selectively form duplex molecules with complementary stretches of other hin47 genes. Depending on the application, a variety of hybridization conditions may be employed to achieve varying degrees of selectivity of the probe toward the other hin47 genes. For a high degree of selectivity, relatively stringent conditions are used to form the duplexes, such as low salt and/or high temperature conditions, such as provided by 0.02M to 0.15M NaCl at temperatures of between about 50° to 70° C. For some applications, less stringent hybridization conditions are required, such as 0.15M to 0.9M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

In a clinical diagnostic embodiment, the nucleic acid molecules encoding the hin47 genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing hin47 gene sequences.

The nucleic acid molecules comprising hin47 genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hin47 genes of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label.

4. Expression of the Genes encoding analogs of Hin47 having reduced protease activity Vectors perhaps containing replicon and control sequences which are derived from species compatible with the host cell may be used for the expression of the Hin47 analog genes as provided herein in expression systems. The vector ordinarily carries a replication site, as well as marking sequences which are capable of providing phenotype selection in transformed cells. For example, E. coli may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems (Chang et al, 1979; Goeddel et al, 1980) and other microbial promoters, such as the T7 promoter system (U.S. Pat. No. 4,952,496). Details concerning the nucleotide sequences of promoters are known, enabling a skilled worker to ligate them functionally with plasmid vectors. The particular promoter used will generally be a matter of choice depending upon the desired results. Hosts that are appropriate for expression of the Hin47 analogs include E. coli, Bacillus species, Haemophilus Bordetella fungi, yeast, mammalian cells or the baculovirus expression system may be used.

Thus, in accordance with the invention, it may be preferred to make the Hin47 analog protein by recombinant methods. Particularly desirable hosts for expression in this regard include Gram positive bacteria which do not have LPS and are therefore endotoxin free. Such hosts include species of Bacillus and may be particularly useful for the production of non-pyrogenic Hin47 analog.

Biological Deposits

Plasmid DS-1011-1-1 (pT7/Hin47*) that contains a portion coding for a Hin47 analog that is described and referred to herein has been deposited with the American Type Culture Collection (ATCC) located at Rockville, Md. USA, pursuant to the Budapest Treaty and prior to the filing of this continuation-in-part application on Jul. 27, 1994 under Accession No. 75845. Samples of the deposited plasmid will become available to the public upon grant of a patent based upon this United States patent application. The invention described and claimed herein is not to be limited in scope by plasmid deposited, since the deposited embodiment is intended only as an illustration of the invention. Any equivalent or similar plasmids that encode similar or equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amploy reported in the scientific literature and are well within the ability of those skilled in the art.

EXAMPLE 1

This Example illustrates the cloning of the hin47 gene from non-typable H. influenzae strain SB33.

Chromosomal DNA was prepared from H. influenzea strain SB33, and an EMBL3 library was prepared and screened with a labelled oligonucleotide probe specific for the 5'-end of hin47. Non-typable H. influenzae strain SB33 was grown on Mueller-Hinton agar or in brain heart infusion broth as described by Harkness et al, 1992. Chromosomal DNA was prepared as follows: cells from 50 ml of culture were pelleted by centrifugation at 5000 rpm for 15 to 20 min, at 4° C., in a Sorvall RC-3B centrigure. The cell pellet was resuspended in 10 ml of TE (10 mM Tris/HCl, 1 mM EDTA, pH 7.5), pronase was added to 500 μg ml$^{-1}$ and SDS to 1%. The sample was incubated at 37° C. until a clear lysate was obtained. The lysate was gently extracted once with Tris-saturated phenol (pH 7.4), once with Tris-saturated phenol/chloroform (1:1) and once with chloroform. The final aqueous phase was dialysed at 4° C. for 24 h against 1M NaCl, followed by 24 h against TE.

An EMBL3 library was prepared by partial digestion of SB33 chromosomal DNA with Sau3A I, followed by size fractionation either on a 10 to 30% sucrose gradient in TNE (20 mM Tris/HCl, 5 mM NaCl, 1 mM EDTA, pH 8.0) or by preparative gel electrophoresis. Fractions containing DNA fragments greater than 5 kb in length were pooled, precipitated and ligated with BamH I arms of EMBL3 (Promega). The ligation mixture was packaged using a Gigapack II packaging kit and plated onto E. coli LE392 cells. The libraries were amplified and stored at 4° C. in the presence of 0.3% chloroform.

Plaques were lifted onto nitrocellulose filters for hybridization with a $^{32}$P-labelled oligonucleotide probe (3026.SL). The oligonucleotide sequence was ATGAAAAAAA-CACGTTTTGTATTAAATAGTATTGCACTTGG (SEQ ID NO: 3) corresponding to the N-terminal amino acid sequence MKKTRFVLNSIALG (SEQ ID NO: 19). Phage DNA was prepared from putative plaques and the insert DNA was excised by Sal I digestion and clones into pUC8-BgXb digested with Sal I. Plasmids JB-1031-1-14 and JP-1068-2-2 (FIG. 1) were selected for further analysis.

EXAMPLE 2

This Example illustrates the characterization and sequence analysis of the hin47 gene and deduced amino acid sequence of the Hin47 protein from NTHi strain SB33.

Restriction mapping and Southern blot analysis of clones JB-103101-14 and JB-1068-2-2 localized the hin47 gene on a 4.7 kb BamH I/BamH I or a 2.7 kb BamH I/Pst I DNA fragment. The 4.7 kb BamH I/BamH I fragment from JB-1068-2-2 was subcloned into pUC8/BgXb generating plasmid DS-755-1. The 3.1 kb BamH I to Xba I fragment of DS-755-1 was subcloned into pUC18 generating plasmid JB-1165-1 which has restriction sites suitable for the Erase-a-base (Promega) procedure (FIG. 1). This technique generates successive clones with increasing truncations of insert DNA, with the deletions occurring from the same end. The resultant nested set of clones can be sequenced rapidly using a universal primer.

DNA from plasmid JB-1165-1 was digested from BamH I and Sac I and subjected to exoIII digestion using an Erase-a-base kit. The resultant set of truncated plasmids was analysed by agarose gel electrophoresis and representative plasmids were selected from sequence analysis.

Plasmid DNA for sequencing was prepared by a modification of the procedure of Holmes and Quigley, 1981. Briefly, the cell pellet from 50 ml of culture was resuspended in 10 ml STET (8% sucrose, 5% Triton X-100, 50 mM EDTA, and 50 mM Tris/HCl, pH 8.0), lysozyme (2.5 mg) was added and the mixture was boiled for 2 min. The sample was spun at 14,000 rpm in a Sorvall RC 5B for 20 minutes and the supernatant was precipitated with an equal volume of isopropanol, washed with 70% ethanol then absolute ethanol, and then air dried. The pellet was resuspended in 0.9 ml of TE, then 20 μl of 5 mg ml$^{-1}$ RNAse A were added, and the mixture was incubated at 37° C. for 15 min. After the addition of 500 μl of 1.5M NaCl/30% PEG, the mixture was incubated on ice for 30 min and the DNA was pelleted by centrifugation in an Eppendorf microfuge for 10 min. The pellet was resuspended in 400 μl of TE and extracted twice with Tris-saturated phenol (pH 7.4), twice with Tris-saturated phenol/chloroform (1:1) and twice with chloroform. The DNA was precipitated by adding 40 μl of 3M ammonium acetate and 1 ml of ethanol, washed with 70% ethanol and resuspended in distilled water.

DNA samples were sequenced using the ABI model 370A DNA sequencer and the dye terminator chemistry. The universal reverse primer was used with the nested set of clones to determine the sequence of the hin47 coding strand. Oligonucleotide primers of approximately 25 bases in length were used to confirm the sequence of the non-coding strand. The nucleotide sequence of the SB33 hin47 gene and the deduced amino acid sequence of the Hin47 protein are shown in FIG. 2. The nucleotide and N-terminal amino acid sequences of Hin47 presented at the ASM meeting, New Orleans, May 26 to 30, 1992 are indicated in lower case on FIG. 2. The amino terminal sequences of the SB33 Hin47 and this presented sequence are identical, establishing the identity of the cloned gene as hin47.

EXAMPLE 3

This Example describes the discovery of serine protease activity of Hin47 protein.

The deduced amino acid sequence of Hin47 protein determined in Example 2 above was compared with all other known proteins in the Genbank data base. As described above, Hin47 protein is described in published PCT applications WO 94/00149, WO 92/11367 and WO 92/10936 to be an adhesin molecule of Haemophilus. It was, therefore, a surprising and unexpected discovery of the present invention that Hin47 protein has significant amino acid homology (55%) with the serine proteases E. coli htrA and S. typhimurium htrA and other proteases. These amino acid sequence homologies are shown in FIGS. 3 and 4. Furthermore, Hin47 protein was found to autodigest unless it was stored in the presence of a serine protease inhibitor, such as Pefablock.

EXAMPLE 4

This Example illustrates the generation of the mutant hin47 gene by site-directed mutagenesis.

As explained above, H. influenzae Hin 47, E. coli htrA, and S. typhimurium htrA are all serine proteases. The consensus sequence of the active site of serine proteases is GDSGGPK (SEQ ID NO: 18) [Brenner, 1988] with serine being the active residue. The htrA proteins both have a GNSGGAL (SEQ ID NO: 17) sequence and in H. influenzae Hin47, there is the identical sequence between residue 195 and 201 of the mature protein. Thus, the serine residue at position 197 was selected for site-directed mutagenesis, to produce an analog of Hin47 with reduced protease activity.

An oligonucleotide CGCTCCACCAGCATTACCGCGG (SEQ ID NO: 20) was synthesized which would change the serine residue at 197 to an alanine. The hin47 gene was cloned into M13mp18 generating clone DS-981-3 and mutagenesis was performed using the Amersham In Vitro Site-Directed Mutagenesis kit. Clone DS-991-S was confirmed by sequence analysis to contain the mutation Serine-197 to Alanine. This mutant hin47 gene is designated hin47*. Using appropriate oligonucleotides, the serine residue at 197 was changed to a cysteine (mutant S197C) and a threonine (mutant S197T).

In addition a comparison of the amino acid sequence of Hin47 with other proteases (as shown in FIG. 4) revealed that amino acids His-91 and Asp-121 are sites appropriate for mutagenesis to produce an analog of Hin47 with reduced protease activity. By mutagenesis methods analogous to those described above, His-91 and/or Asp-121 are deleted or replaced by different amino acids. Such amino acid replacements included His-91 to Alanine (mutant H91A) and Arginine (mutant H91R) and Asp-121 to Alanine "(mutant D121A) and Glutamic acid (mutant D121E)". Oligonucleotides to effect such mutagenesis included:

His-91→Ala-91 5' ATCAATAACAGCATTATTGGT 3' (SEQ ID NO: 21)

Asp-121→Ala-121 5' TAATGCAATTGCTGATAGTTC3' (SEQ ID NO: 22). Corresponding olitonucleotides were employed to effect other mutations. Multiple mutations also were effected in which His-91 and Serine-197 both were replaced by Alanine (mutant H91A/S197A) and His91, Asp-121 and Ser-197 were all replaced by Alanine (mutant H91A/D121A/S197A).

These additional mutants were produced, extracted purified and tested for protease activity as described for the Hin47* material in the succeeding Examples.

Many serine proteases are secreted in an inactive ('zymogen') form, and require clipping to expose their active sites. N terminal sequence analysis of mature natural Hin47 protein suggested the cleavage of the preprotein to occur at KFFFG DRFAEQ (SEQ ID NO: 23). Modifications of amino acids that prevent cleavage of the molecule to produce the active protease molecule can produce an analog of Hin47 having reduced protease activity.

EXAMPLE 5

This Example illustrates the construction of plasmids expressing Hin47 Ser-197→alanine analog from *E. coli*.

The mutated hin47* gene from plasmid DS-991-8 was cloned into the pT7-7 expression vector to generate plasmid DS-1011-1-1 (FIG. 5). *E. coli* strain BL21/DE3 was transformed to generate *E. coli* strain DS-1018-3-1 which expresses Hin47 Ser-197→alanine analog upon induction.

In order to utilize tetracycline selection, the hin47* gene was cloned into pBR328. The Bgl II/Cla I T7/hin47* gene fragment from DS-1011-1-1 was cloned into pEVvrf1 (Young and Davis, 1985) in order to generate a Bgl II/BamH I fragment which could be cloned into pUC-4K (Pharmacia) digested with BamH I. The resultant clone DS-1034-3 was digested with EcoR I and the T7/hin47* gene fragment cloned into pBR328 (Boehringer Mannheim Corporation) to generate plasmids DS-1048-2 and DS-1067-2. Electroporation of plasmid DNA into *E. coli* strain BL21/DE3 resulted in strains DS-1071-1-1 and DS-1071-3-1 which express the Hin47 Ser-197→alanine analog.

EXAMPLE 6

This Example illustrates the expression of Hin47 Ser-197→alanine analog from *E. coli*.

An overnight culture of strains DS-1018-3-1, DS-1071-1-1, or DS-1071-3-1 were grown overnight in NZCYM media+3% dextrose+antibiotics (ampicillin at 25 $\mu$g ml$^{-1}$ or tetracycline at 10 $\mu$g ml$^{-1}$), at 37° C., with shaking. A 1:40 dilution of the overnight culture was inoculated into the same medium and grown at 37° C. with shaking until the absorbance was $A_{578}$ approximately 0.3. A $\frac{1}{10}$ volume of 10% lactose was then added to induce expression from the T7 promoter. Cell samples were harvested about 4 hours after induction by centrifuging culture samples at 5000 rpm for 10 min in a Sorvall RC-3B, at 4° C.

EXAMPLE 7

This Example illustrates the extraction and purification of Hin47.

Hin47 was expressed as soluble protein in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000×g and the resulting supernatant which contained >95% of the soluble Hin47 protein was retained. This fraction was called "Hin47-extract".

This Hin47-extract was further purified on a DEAE Sephacel column. Forty ml of the Hin47-extract was applied onto a 20-ml DEAE Sephacel column equilibrated in 50 mM Tris-HCl, pH 8.0. Hin47 bound to the column under these conditions. The column was washed with 100 ml of 50 mM Tris-HCl, pH 8.0, and then washed with 100 ml of 50 mM Tris-HCl, pH 8.0 containing 20 mM NaCl. Hin47 was then eluted with 50 mM Tris-HCl, pH 8.0, containing 40 mL NaCl. The amount of Hin47 in the fractions was determined by the BCA protein assay. The purity of Hin47 was assessed SDS-PAGE analysis. The fractions containing Hin47 were combined and stored at −20° C.

Only the H91A mutant was as soluble as the wild-type Hin47 protein, most of the other mutants being produced as inclusion bodies.

EXAMPLE 8

This Example illustrates the extraction and purification of Hin47 Ser-197→alanine analog.

Hin47 Ser-197→alanine analog was expressed in inclusion bodies in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000×g and the resulting pellet was saved. The pellet was re-extracted with 40 ml of 50 mM Tris-HCl, 0.5% Triton X-100, 10 mM EDTA, pH 8.0. The suspension was sonicated 10 min at 70% duty circle. The extract was centrifuged at 300×g for 5 min. The resultant supernatant was centrifuged again at 20,000×g for 30 min and the resultant pellet was saved. The pellet was resuspended in 50 mM Tris-HCl, 0.5% Triton X-100, 10 mM EDTA, pH 8.0. The suspension was then mixed with 50 mM Tris-HCl, pH 8.0 containing 8M urea. The final urea concentration in the mixture was adjusted to 2M with 50 mM Tris-HCl, pH 8.0. Hin47 Ser-197→alanine analog was completely solubilized under these conditions. The final volume of the solution was 20 ml. This fraction is called "Hin47 analog-extract". The Hin47 analog-extract was further purified on a DEAE Sephacel column. Twenty ml of Hin47 analog-extract was applied onto a 10 ml DEAE Sephacel column equilibrated in 50 mM Tris-HCl, pH 8.0. Hin47 Ser-197→alanine analog bound to the column under these conditions. The column was washed with 50 mM Tris-HCl, pH 8.0, and Hin47 analog was eluted with 50 mM Tris-HCl, pH 8.0, containing 30 mM NaCl. The amount of Hin47 analog in the fractions was determined by the BCA protein assay. The purity of Hin47 analog was assessed by SDS-PAGE analysis (FIG. 6). The fractions containing Hin47 analog were combined and stored at −20° C.

EXAMPLE 9

This Example illustrates the protease activity of Hin47 and Hin47 Ser-197→alanine analog.

The enzymatic activity of Hin47 and Hin47 Ser-197→alanine analog was analyzed using β-casein as a substrate (FIG. 7). The reaction mixtures contained 5 μg of β-casein and either Hin47 or Hin47 analog. The reaction was carried out at 37° C. for two hours, and then stopped by adding the SDS-sample buffer and instantly heating the sample at 100° C. for 5 min. The aliquots were analyzed by SDS-PAGE. As shown in FIG. 7, digestion of β-casein by Hin47 was more obvious after two hours (panel A, lane 1) in comparison to the fractions containing Hin47 analog (panel A, lane 2) or without any exogenous proteins (panel A, lane 3). The presence of Hin47 or Hin47 analog in these mixtures were confirmed by immuno-blotting using a monoclonal antibody to Hin47 (FIG. 7, panel C, lanes 1 and 2).

The protease activities of Hin47 and Hin47 Ser-197→alanine analog were also compared by analyzing the autodigestion of Hin47 or Hin47 analog at 4° C. and −20° C. The purified Hin47 or analog were stored at either 4° C. or −20° C. for up to 20 days. Aliquots were taken on days 0, 10 and 20 and the stability of Hin47 or analog was analyzed by immuno-blotting using a Hin47 monoclonal antibody (FIG. 8). The analog was much more stable than Hin47 up to 20 days when stored at either 4° C. or −20° C.

To further examine the protease activity of the Hin47 Ser-197→alanine analog, the ability of Hin47 or analog to degrade an 80-kDa H. influenzae recombinant antigen was examined. Thus, a mixed antigen study was performed to determine the proteolytic effect of Hin47 or Hin47 analog on another antigen. An 80 kDa H. influenzae recombinant protein (TBP1) was chosen for this study in order to distinguish it from the Hin47 or analog protein (47 kDa). Five mixtures were formulated as follows: 80-kDa protein alone; 80-kDa protein+Hin47; 80-kDa protein +analog; Hin47 alone; and analog alone. The amount of each protein in the mixture was 5 μg. The mixtures were stored at 4° C. up to four weeks. Aliquots were taken on days 0, 7, 14 and 28 for analysis by SDS-PAGE (FIG. 9). Both the 80 kDa protein and Hin47 were largely degraded after one week (lanes 2 and 4). In contrast, the 80 kDa protein in combination with Hin47 analog remained intact after one week, and showed only slight degradation even after four weeks (lane 3).

The residual protease activity of other Hin47 analogues was assessed using the digestion of β-casein as described by Lipinska et al (ref. 13) and the results of which are shown in Table 3. Only one mutant (D121E) was found to retain serine protease activity.

EXAMPLE 10

This Example illustrates the comparative immunogenicity of Hin47 and Hin47 analog in mice.

The results of a study to determine the comparative immunogenicity of Hin47 and the Hin47 Ser-197→alanine analog are shown in FIG. 10. Thus, groups of five Balb/c mice were injected three times (as indicated by arrows) s.c. on days 1, 29 and 43 with 1-μg dose of either Hin47 or Hin47 analog in the presence of AlPO$_4$ (1.5 mg per dose). Blood samples were taken on days 14, 28, 42 and 56 (as indicated by bleeds 1, 2, 3 and 4, respectively) for analyzing the anti-Hin47 antibody titers by EIAs. The determination of anti-Hin47 antibodies in mouse sera was performed as described by Panezutti et al. (1993). Microtiter wells were coated with 1 μg of either Hin47 or analog for 16 hours at room temperature. The plates were then blocked with 0.1% (w/v) bovine serum albumin in PBS. The mouse sera were serially diluted, added to the wells, then incubated for one hour at room temperature. Affinity-purified F(ab')$_2$ fragments of goat anti-mouse IgG (Fc specific) antibody conjugated to horseradish peroxidase were used as the second antibody. The reactions were developed using tetramethylbenzidine (TMB/ H$_2$O$_w$) and absorbencies were measured at 450 nm (using 540 nm as a reference wavelength) in a Flow Multiskan MCC microplate reader. The reactive titer of an antiserum was defined as the reciprocal of the dilution consistently showing a two-fold increase in absorbance over that obtained with the pre-bleed serum sample. As can be seen from FIG. 10, both Hin47 and the Hin47 analog elicited comparable IgG titers in mice regardless of whether Hin47 or mutant was used as an antigen in EIAs.

Immunogenicity studies were also performed using the H91A Hin47 analogue. This analogue was found to produce an immune response equivalent to that of the S197A Hin47 analogue.

To further examine the immune response to Hin47 or the Hin47 Ser-197→alanine analog, the subclasses of anti-Hin47 IgG in mouse sera were determined. Microtiter wells were coated with 1 μg of purified Hin47 or analog. The final bleed of mouse serum samples from the comparative immunogenicity study (as described above) were pooled and tested in EIAs. Rat anti-mouse IgG$_1$, IgG$_{2a}$, IgG$_{2b}$ antibodies conjugated horseradish peroxidase and rabbit anti-mouse IgG$_3$ conjugated to horseradish peroxidase were used as reagents in EIAs. The working dilution of each conjugate was determined using purified antibody subclasses to avoid cross reactivity. The reactive titers were determined as described above. As shown in Table 1 below, the IgG-subclass profile induced in mice by either Hin47 or Hin47 analog were identical, regardless of whether Hin47 or analog was used as a solid antigen in the EIAs. The predominant IgG response in both groups of mouse sera was of the IgG$_1$ isotype. Hence, the Hin47 analog exhibited substantially the same immunogenic properties as the natural protein.

EXAMPLE 11

This Example illustrates the immunoprotective properties of Hin47 and Hin47 Ser-197→alanine analog.

The immunoprotective properties of Hin47 and the Hin47 Ser-197→alanine analog were analyzed by the ability of Hin47 specific antisera to protect infant rats against H. influenzae type b strain MinnA in a bacteremia model. The results of this study are shown in Table 2 below. Groups of nine 6-day old Wistar infant rats were inoculated subcutaneously (s.c.) on the dorsum close to the neck with 0.1 mL of either a rabbit anti-Hin47 analog antiserum or the corresponding prebleed serum. Twenty-four hours later, the animals were challenged intraperitoneally (i.p.) with 700 cfu of freshly grown Hib strain MinnA. Blood samples were collected 20 hours post-challenge and plated onto chocolate agar plates. Bacterial colonies were counted after 24 hours. As shown in Table 2, three out of nine animals in the group inoculated with anti-Hin47 analog antiserum did not show any bacteremia in their blood. Only one mouse in the group inoculated with anti-Hin47 analog antiserum (11%) had a higher bacteria recovery from the blood sample compared to mice inoculated with prebleed serum. In contrast, bacteria were recovered from all the nine mice inoculated with pre-bleed serum. Four out of nine animals (44%) in the group inoculated with pre-bleed serum showed high levels (500 to 1,000) of bacteria recovered in blood samples.

The infant rat model of bacteremia, was used to assess the protection afforded by anti-Hin47 or anti-Hin47 mutant antisera against bacteremia caused by H. influenzae type b infection. 9/10 infant rats were protected by antisera raised against each of wild-type Hin47, H91A Hin47, and S197A Hin47 analogues.

EXAMPLE 12

This Example illustrates the induction of Hin47 under stress conditions.

*H. influenzae* strain Eagan was grown at 37° C. to an $A_{590} \approx 0.3$ in brain heart infusion broth (BHI) containing hemin (2 μg ml$^{-1}$) and NAD (2 μg ml$^{-1}$). The sample was aliquotted and grown at 37° C., 42° C., 43.5° C., or in the presence of 6% ethanol, 0.2M NaCl, or 0.3M NaCl. *E. coli* strain JM109 was grown at 37° C. to an $A_{590}$ of ≈0.3 in YT media and aliquotted as described. Samples were collected at 9 min, 20 min, 40 min, 60 min, and 9 min and analyzed by OD and SDS-PGE/Western blot. Guinea pig antisera which recognized both *H. influenzae* Hin47 and *E. coli* htrA was used for Western blot analysis. The *E. coli* htrA protein was produced in large quantities when the organism was grown at 43.5° C. and a small amount of the *H. influenzae* Hin47 protein can be observed. With growth in media containing 6% ethanol, both the *E. coli* htrA and the *H. influenzae* Hin47 proteins are induced. The high salt conditions were insufficient to induce either protein. These results indicate that Hin47 is a stress response protein in *H. influenzae,* inducible under similar conditions to the *E. coli* htrA protein.

EXAMPLE 13

This Example illustrates the purification of the H91A Hin47 protein.

The soluble H91A mutant was purified essentially as described for the wild-type Hin47 in Example 7, with the addition of a hydroxylapatite (HAP) column. The HAP column was equilibrated in 10 mM sodium phosphate buffer (pH 8.0) and the run-through from the DEAE column was loaded. The H91A Hin47 bound to the Hap column and contaminating proteins were removed by washing the column with 175 mM sodium phosphate buffer. The H91A Hin47 protein was eluted with 300 mM sodium phosphate buffer (pH 8.0) and stored at −20° C.

EXAMPLE 14

This Example illustrates the protection studies with Hin47 and Hin47 mutants in the chinchilla model of otitis media.

The chinchilla model of otitis media (ref. 14) was used to assess the protection induced by active immunization with wild-type Hin47, H91A Hin47, or S197A Hin47.

Chinchillas (~500 g weight) were immunized i.m. three times with 30 μg/dose of Hin47 or Hin47 mutant (H91A or S197A) adjuvanted in AlPO4, on days 1, 28 and 42. The animals were challenged on day 56, through the bulla, with 50–1000 cfu of virulent NTHi strain SB12 organisms. Animals were monitored by tympanometry and otoscopic examination and at 4 days post-challenge, middle ear fluids were aspired and plated on chocolate agar. Bacterial colonies were counted after 24 h. The wild-type Hin47 and H91A Hin47 proteins afforded protection to ~50% of the animals, but the S197A Hin47 was non-protective in this model (Table 3).

SUMMARY OF DISCLOSURE

In summary of this disclosure, the present invention provides novel analogs of *Haemophilus influenzae* Hin47 protein which have a decreased protease activity of less than about 10% of that of the natural Hin47 protein as well as isolated and purified DNA molecules encoding the same.

TABLE 1

| | Hin47 IgG titers in mouse immune sera | | | |
|---|---|---|---|---|
| | IgG titers in Group #1* | | IgG titers in Group #2* | |
| IgG Suclass | To Hin47 | To Mutant | To Hin47 | To Mutant |
| IgG (H + L) | 102,400 | 102,400 | 102,400 | 102,400 |
| IgG$_1$ | 25,600 | 25,600 | 25,600 | 25,600 |
| IgG$_{2a}$ | <100 | <100 | <100 | <100 |
| IgG$_{2b}$ | 400 | 400 | 400 | 400 |
| IgG$_3$ | <100 | <100 | <100 | <100 |

*Group #1: Immune sera were pooled from a group of five mice received Hin47 immunization.
*Group #2: Immune sera were pooled from a group of five mice received Hin47 mutant immunization.

Group #1: Immune sera were pooled from a group of five mice received Hin47 immunization.

Group #2: Immune sera were pooled from a group of five mice received Hin47 mutant immunization.

Plates were coated with either Hin47 or mutant protein.

TABLE 2

| Protective ability of rabbit Anti-Hin47 Mutant antiserum against Hib in infant rat model of bacteremia | | | | | |
|---|---|---|---|---|---|
| | | Number of Animals cfu of Bacteria/2.5 μL Blood | | | |
| Antibody | Av. 0 | Av. 50 (10–100) | Av. 200 (100–300) | Av. 650 (300–1,000) | Total Animals |
| Anti-Hin47* | 3 | 3 | 2 | 1 | 9 |
| Prebleed | 0 | 4 | 1 | 4 | 9 |

Groups of nine 6-day old infant rats were immunized s.c. with either a rabbit anti-Hin47 mutant antiserum or the corresponding prebleed serum. Animals were challenged i.p. with 700 efu *H. influenzae* strain MinnA after 24 hours. The blood samples were taken at 20 hours after the challenge.

Anti-Hin47* antibody: rabbit immune serum raised against purified Hin47 mutant in CFA/IFA.

Average bacteria recovery from immunized group: 100 cfu per 2.5 μL of blood; from control group: 290 cfu per 2.5 μL of blood.

TABLE 3

| Characterization of Hin47 mutants | | | | |
|---|---|---|---|---|
| Mutant | Protease[a] | Solubility[b] | Protection - rat[c] | Protection - chinchilla[d] |
| WILD-TYPE | + | + | + | ± |
| H91A | − | + | + | ± |
| H91R | − | − | ND[e] | ND |
| D121A | − | − | ND | ND |
| D121E | + | − | ND | ND |
| S197A | − | − | + | − |
| S197C | − | ± | ND | ND |
| S197T | − | ± | ND | ND |
| H91A/S197A | − | − | ND | ND |
| H91A/D121A/S197A | − | − | ND | ND |

[a]Protease activity is measured by the ability to digest the substrate β-casein.
[b]Solubility indicates production as a soluble protein (+) or inclusion bodies (−).
[c]Protection in the infant rat passive model of bacteremia.
[d]Protection in the chinchilla model of otitis media.
[e]ND is not determined

REFERENCE LIST

1. Zangwill et al, 1993 MMWR 42:1–15.
2. Schoendorf et al, 1994 Pediatrics 93:663–8.
3. Brenner et al, 1988 Nature 334:528–530.
4. O'Hagan 1992 Clin. Pharmokinet. 22:1–10.
5. Ulmer et al, 1993 Curr. Opinion. Invest. Drugs 2:983–989.
6. Chang et al, 1978 Nature 275:617.
7. Goeddel et al 1980 Nucl. Acid. Res. 8:4057.
8. Harkness et al, 1992 J. Bacteriol. 174:2425–2430.
9. Loeb et al, 1987 Infec. Immun. 55:2612–2618.
10. Holmes and Quigley 1981. Analyt. Biochem. 114:193–197.
11. Young and Davis 1985 Gene 38:31–38.
12. Panezutti et al, 1993 Infec. Immun. 61:1867–72.
13. Lipinska et al, 1985 Bacteriol. 171:1574–1584.
14. Barenkamp et al, 1986 Infect. Immun. 52:572–578.

What we claim is:

1. An isolated and purified analog of *Haemophilus influenzae* Hin47 protein wherein multiple amino acids of the natural Hin47 protein contributing to protease activity have been deleted or replaced by different amino acids, to provide a reduced protease activity which is less than 10% of that of the natural Hin47 protein.

2. The analog of claim 1 having substantially the same immunogenic properties as natural Hin47 protein.

3. The analog of claim 1 wherein at least one deleted or replaced amino acid is selected from amino acids 195 to 201 of natural Hin47 protein.

4. The analog of claim 3 wherein said at least one amino acid is Serine-197.

5. The analog of claim 4 wherein Serine-197 is replaced by alanine, cysteine or threonine.

6. The analog of claim 1 wherein at least one amino acid is Histidine-91 or Asp-121 of natural Hin47 protein.

7. The analog of claim 6 wherein Histidine-91 is replaced by alanine, lysine or arginine.

8. The analog of claim 6 wherein Asp-121 is replaced by alanine.

9. The analog of claim 1 wherein the multiple amino acids are His-91 and Ser-197 and are deleted or replaced by alanine.

10. The analog of claim 1 wherein the multiple amino acids are His-91, Asp-121 and Ser-197 and are deleted or replaced by alanine.

11. An isolated and purified nucleic acid molecule comprising a mutant *Haemophilus influenzae* hin47 gene encoding an analog of *Haemophilus influenzae* Hin47 protein having a decreased protease activity which is less than about 10% of that of natural Hin47 protein, wherein multiple codons of a wide-type hin47 gene encoding multiple amino acids contributing to protease activity have been deleted or replaced by codons encoding different amino acids to form said mutant hin47 gene.

12. The nucleic acid molecule of claim 11 wherein said encoded analog has substantially the immunogenic properties of natural Hin47 protein.

13. The nucleic acid molecule of claim 11 wherein at least one deleted or replaced codon encodes at least one amino acid from amino acids 195 to 201 of natural Hin47 protein.

14. The nucleic acid molecule of claim 13 wherein the at least one codon is that encoding Serine-197.

15. The nucleic acid molecule of claim 14 wherein the codon encoding Serine-197 is replaced by a codon encoding alanine, cysteine or threonine.

16. The nucleic acid molecule of claim 11 wherein at least one codon encodes His-91 or Asp-121 of natural Hin47 protein.

17. The nucleic acid molecule of claim 16 wherein the codon encoding His-91 is replaced by a codon encoding alanine, lysine or arginine.

18. The nucleic acid molecule of claim 16 wherein the codon encoding Asp-121 is replaced by a codon encoding alanine.

19. The nucleic acid molecule of claim 15 wherein said mutant gene is formed by site-directed mutagenesis of a wild-type hin47 gene.

20. The nucleic acid molecule of claim 12 wherein the multiple codons encode His-91 and Ser-197 and are deleted or replaced by codons encoding alanine.

21. The nucleic acid molecule of claim 12 wherein the multiple codons encode His-91 Asp-12 and Ser-197 and are deleted or replaced by codons encoding alanine.

22. A recombinant plasmid adapted for transformation of a host comprising a plasmid vector into which has been inserted the nucleic acid molecule of claim 11.

23. A transformed cell containing the recombinant plasmid of claim 22.

24. A method for producing an analog of *Haemophilus influenzae* Hin47 protein having a reduced protease activity which is less than about 10% of natural Hin47 protein, which comprises:

identifying multiple amino acids residues of Hin47 protein which contribute to protease activity thereof;

effecting site-directed mutagenesis of the hin47 gene to remove or replace nucleotide sequences encoding said multiple amino acids and to produce a mutated hin47 gene;

introducing the mutated hin47 gene into a cell to produce a transformed cell; and growing the transformed cell to produce the Hin47 analog.

25. The method of claim 24 wherein at least one amino acid is selected from amino acids 95 to 201 of natural Hin47 protein.

26. The method of claim 25 wherein at least one amino acid is Serine-197.

27. The method of claim 25 wherein Serine-197 is replaced by alanine, cysteine or threonine.

28. The method of claim 24 wherein said at least one amino acid is Histidine-91 or Asp-121 of natural Hin47 protein.

29. The method of claim 28 wherein Histidine-91 is replaced by alanine, lysine or arginine.

30. The method of claim 28 wherein Asp-121 is replaced by alanine.

31. The method of claim 24 wherein the multiple amino acids are His-91 and Ser-197 and are deleted or replaced by alanine.

32. The method of claim 24 wherein the multiple amino acids are His-91, Asp-121 and Ser-197 and are deleted or replaced by alanine.

33. The method of claim 24 wherein said introduction of the mutated hin47 gene produces a transformed cell in which the mutated hin47 gene is under control of the T7 promoter, and said growing of said transformed cell and expression of the Hin47 analog by said T7 promoter is effected by culturing in an inducing concentration of lactose.

34. A method of providing an isolated and purified *Haemophilus influenzae* Hin47 analog, which comprises:

identifying multiple amino acids residues of Hin47 protein which contribute to protease activity thereof;

effecting site-directed mutagenesis of the hin47 gene to remove or replace nucleotide sequences encoding said multiple amino acids and to produce a mutated hin47 gene;

introducing the mutated hin47 gene into a cell to produce a transformed cell; and growing the transformed cell to produce grown transformed cells harbouring inclusion bodies containing the Hin47 analog;

disrupting said grown transformed cells to produce supernatant and said inclusion bodies;

solubilizing said inclusion bodies to produce a solution containing Hin47 analog;

chromatographically purifying said Hin47 analog from said solution free from cell debris; and isolating said purified Hin47 analog.

35. The method of claim 34 wherein said introduction of the mutated hin47 gene produces a transformed cell in which the mutated hin47 gene is under control of the T7 promoter, and said growing of said transformed cell and expression of the Hin47 analog by said T7 promoter are effected by culturing in an inducing concentration of lactose.

36. A chimeric molecule, comprising an analog as claimed in claim 1 linked to a polypeptide, protein or a polysaccharide.

37. The method of claim 34 wherein at least one amino acid of said identified multiple amino acids is selected from amino acids 95 to 201 of natural Hin47 protein.

38. The method of claim 37 wherein said at least one amino acid is Serine-197.

39. The method of claim 37 wherein Serine-197 is replaced by alanine, cysteine or threonine.

40. The method of claim 34 wherein at least one amino acid of said identified multiple amino acids is Histidine-91 or Asp-121 of natural Hin47 protein.

41. The method of claim 40 wherein Histidine-91 is replaced by alanine, lysine or arginine.

42. The method of claim 40 wherein Asp-121 is replaced by alanine.

43. The method of claim 34 wherein multiple amino acids are deleted or replaced.

44. The method of claim 34 wherein the multiple amino acids are His-91 and Ser-197 and are deleted or replaced by alanine.

* * * * *

UNITED STATES PATENT AND TRADEMARK OFFICE
CERTIFICATE OF CORRECTION

PATENT : 5,869,302

DATED : February 9, 1999

INVENTOR(S) : Sheena M. Loosmore et al

It is certified that error appears in the above-identified patent and that said Letters Patent is hereby corrected as shown below:

In the drawings, Sheet 13 consisting of Fig. 4B, should be deleted to be replaced with Sheet 13 consisting of the corrected Fig. 4B, as shown on the attached page.

Signed and Sealed this

Eleventh Day of July, 2000

*Attest:*

Q. TODD DICKINSON

*Attesting Officer*    *Director of Patents and Trademarks*

FIG. 4B

```
SGBE   :                 TYYFITAGHCT--D------GATT-WWA----------NS-ARITVL
SGA    :                 VAHAITAGHCT-------------NISASW----------------SI
ALP    :                 TKGFVTAGHGIVN-------AT-AR-IG---------------GAVVG
Sal.T: KGYVVINHVDNASVIKVQLSDGR
hin47: KGYVLINNHVIDEA      DK-IT-VQ-----------LQDGRE
              ******* con          >-----------<       >-----X--<      <------->       <--
```

```
                                    # (Asp102)
TQN   : RQS--FRHPDYIPLI¦PVHDH---SNDIMLHISEPADITGGVKV--------
PKAAB : TAD--FPHPGNI SAD-GKDY---SHIDIMLIRLQSPAKITDAVKV--------
PIN   : SKS--IVHPSYN----------SNTL---NNDIMLIKLKSAASLNSRVAS----
CHAA  : AKV--FKNSKYN----------SLITI--NNDITILIKLSTAASFSQIVSA---
EST   : QKI--VVHPYWN----------TDDVAAGYDIALIRLAQSVTINSYVQL----
RP2A  : EKQ--IIHESYN----------SVFN--LHDIMLKEKKVELTPAVNV------
SGT   : TKV--LQAPGYN----------G-T---GKDWALIKLAQPIN-------QPT--
SGBE  : GIT--SGS-SF-----------------FNNDYGIVRYINITITPK      DGTVG
SGA   : GTR--TGT-SF-----------------FNNDYGIIRHSNPAAA       DGRVYLYNGS---
ALP   : -TFAARV--F------------------PGNDRAWSLTSAQIL----LPRVANGSS---
hin47 : FKAKLVG      KDEL     SDIALVQLEKPSNL     TEIKFADSDKLRVGDF
                                 ********** con   >--X--<    >-----<          >-----X--<     <-------->
```